United States Patent

Ueno et al.

Patent Number: 6,159,974
Date of Patent: Dec. 12, 2000

[54] LDL RECEPTOR GENE EXPRESSION PROMOTERS

[75] Inventors: Yoshihide Ueno, Osaka; Koji Morishita, Nishinomiya; Masami Muraoka, Toyonaka; Naohito Ohashi, Takatsuki, all of Japan

[73] Assignee: Sumitomo Pharmaceuticals Company, Limited, Osaka-fu, Japan

[21] Appl. No.: 09/381,829

[22] PCT Filed: Mar. 23, 1998

[86] PCT No.: PCT/JP98/01225

§ 371 Date: Sep. 24, 1999

§ 102(e) Date: Sep. 24, 1999

[87] PCT Pub. No.: WO98/42686

PCT Pub. Date: Oct. 1, 1998

[30] Foreign Application Priority Data

Mar. 24, 1997 [JP] Japan ................................ 9-090208

[51] Int. Cl.$^7$ .................... C07D 25/22; C07D 401/12; A61K 31/53; A61P 3/06
[52] U.S. Cl. ............................. 514/242; 544/182
[58] Field of Search ...................... 544/182, 242

[56] References Cited

U.S. PATENT DOCUMENTS

| 5,187,161 | 2/1993 | Goto et al. | 514/255 |
| 5,571,816 | 11/1996 | Kampe et al. | 514/325 |

FOREIGN PATENT DOCUMENTS

| 55879 | 9/1993 | European Pat. Off. . |
| 63-225366 | 9/1988 | Japan . |
| 90 09985 | 9/1990 | WIPO . |

OTHER PUBLICATIONS

Shoetsu Konno et al., Yakugaku Zasshi, vol. 112, No. 10, pp. 729–741 (1992).
Konno et al., Heterocycles, 26, 3259–3264 (1987).
Konno et al., Chemical Abstract, 109:109970 (1988).
Konno, S. et al., vol. 26, (No. 12) pp. 3259–3264, (1987).
Neunhoeffer, H. et al., Liebigs Ann. Chem.; 1990 (No. 7), pp. 631–640.
Chemical Abstracts vol. 124 (No. 13), Mar. 25, 1996, pp. 1288–1289.

*Primary Examiner*—Mukund J. Shah
*Assistant Examiner*—Thomas McKenzie
*Attorney, Agent, or Firm*—Birch, Stewart, Birch & Kolasch LLP

[57] ABSTRACT

LDL receptor gene expression promoters containing a 1,2,4-triazine derivative of the formula (I):

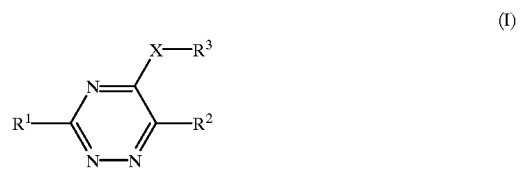

wherein $R^1$ is optionally substituted phenyl or heterocycle; $R^2$ is optionally substituted phenyl, naphthyl, aralkyl, 5- or 6-membered aromatic heterocycle, alkyl, or alkenyl; X is O, S or $NR^4$; $R^3$ is optionally substituted phenyl, naphthyl, aralkyl, 5- to 6-membered aromatic heterocycle, alkyl, cycloalkyl or alkenyl, provided that when X is $NR^4$, then it may form an optionally substituted nitrogen-containing heterocycle, or a pharmaceutically acceptable salt thereof, which can increase the expression dose (the amount of mRNA) of LDL receptor gene, and thus increase the amount of LDL receptor, and reduce the serum cholesterol level, and are useful in the treatment of hyperlipidemia.

8 Claims, No Drawings

LDL RECEPTOR GENE EXPRESSION PROMOTERS

This application is the national phase under 35 U.S.C. §371 of PCT International Application No. PCT/JP98/01225 which has an International filing date of Mar. 23, 1998, which designated the United States of America.

TECHNICAL FIELD

The present invention relates to an LDL receptor gene expression promoter, which are useful in the treatment of hyperlipidemia. More particularly, the present invention relates to a novel 1,2,4-triazine derivative having an activity for promoting expression of LDL receptor gene.

BACKGROUND OF THE INVENTION

It has been known that a low density lipoprotein (LDL) receptor in hepatic cells plays an important role in the regulation of cholesterol level in the blood. That is, a 3-hydroxy-3-methylglutaryl coenzyme A (HMG-CoA) reductase inhibitor inhibits the synthesis of cholesterol in hepatic cells, by which the expression of LDL receptor is indirectly promoted. As a result, the uptake of LDL by a LDL receptor from the blood is increased, and then the cholesterol level in the blood is reduced.

In addition, 1,2,4-triazine derivatives are disclosed, for example, in Liebigs Annalen der Chemie, p. 631, 1990; Chemical and Pharmaceutical Bulletin, p. 926, 1973; Yakugaku-Zasshi, vol. 112, p. 729, 1992; Journal of Organic Chemistry, vol. 52, p. 4287, 1987; Japanese Patent Publication No. 63-225366; Japanese Patent Publication No. 5-45816, etc., but these derivatives have not been known as an LDL receptor gene expression promoter or as an agent for treatment of hyperlipidemia.

DISCLOSURE OF INVENTION

HMG-COA reductase inhibitors have been highly valued in the clinical field as an agent for reducing the blood cholesterol level. However, HMG-COA reductase inhibitors cannot sufficiently reduce the blood cholesterol level to the desired lower level in patients with familial hypercholesterolemia or in patient with coronary artery diseases. Under these circumstances, it is desired to develop an antihyperlipidemic agent showing more effective reducing activity of LDL level in the blood in such patients.

While HMG-COA reductase inhibitors indirectly promote the synthesis of LDL receptors by inhibition of cholesterol synthesis, an LDL receptor gene expression promoter can be expected to show more potent reducing activity of LDL level in the blood by more directly promoting the synthesis of LDL receptors.

In the upstream of each gene of LDL receptor, there is a sequence named SRE (Sterol Regulatory Element), of which transcription is regulated by a free cholesterol in the cells (cf., Goldstein & Brown, Nature, vol. 343, p. 425, 1990). Recently, SREBPs (SRE binding proteins) were identified as substances binding to the SRE of LDL receptor gene (cf., Goldstein, Brown, et al., The Journal of Biological Chemistry, vol. 268, p. 14497, 1993), and it has been reported that the transcription of LDL receptor gene is activated by the SREBP's binding to the SRE of LDL receptor gene (cf., Goldstein, Brown, et al., Cell, vol. 75, p. 187, 1993 and Proceeding of the Natural Academy of Science, vol. 90, p. 11603, 1993). Based on these findings, it is possible to develop a medicament with a completely new mechanism showing an activity of reducing the cholesterol level in the blood by selectively activating the expression of LDL receptor.

The present invention provides an LDL receptor gene expression promoter, which either directly or indirectly regulates the synthesis of LDL receptor with respect to gene transcription, and is useful in the treatment of hyperlipidemia. The present invention also provides a novel compound, which is useful in the regulation of the synthesis of LDL receptor, in the reduction of LDL cholesterol level in the blood, and in the treatment or prevention of arteriosclerosis.

That is, the present invention relates to an LDL receptor gene expression promoter which comprises a 1,2,4-triazine derivative of the formula (I):

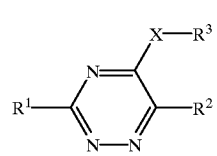

(I)

wherein $R^1$ is a substituted or unsubstituted phenyl group, or a substituted or unsubstituted heterocyclic group, $R^2$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted alkyl group, or a substituted or unsubstituted alkenyl group, X and $R^3$ are the following (i) or (ii):

(i) X is an oxygen atom or a sulfur atom, and $R^3$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted alkyl group, a substituted or unsubstituted cycloalkyl group, or a substituted or unsubstituted alkenyl group;

(ii) X is a group of the formula: —$NR^4$— ($R^4$ is a hydrogen atom, or a substituted or unsubstituted alkyl group), and $R^3$ is the same as defined above, or $R^4$ and $R^3$ may combine together with the nitrogen atom to which they bond to form a substituted or unsubstituted nitrogen-containing heterocyclic group, or a pharmaceutically acceptable salt thereof.

The present invention also relates to (a) a method of promoting expression of LDL receptor gene by administering a 1,2,4-triazine derivative of the formula (1):

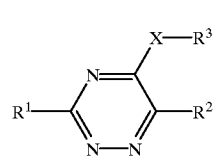

(I)

(wherein $R^1$, $R^2$, $R^3$ and X are the same as defined above) or a pharmaceutically acceptable salt thereof, to a mammal, and (b) use of the said compound (1) or a pharmaceutically acceptable salt thereof in the preparation of a pharmaceutical composition being useful in promotion of LDL receptor gene expression.

Moreover, the present invention also relates to a novel 1,2,4-triazine derivative of the above formula (1) wherein $R^1$ is a substituted or unsubstituted nitrogen-containing aromatic heterocyclic group, $R^2$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted alkyl group, or a substituted or unsubstituted alkenyl group, X is an oxygen atom or a sulfur atom, X and $R^3$ are the following (i) or (ii) ((i) $R^3$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted alkyl group, a substituted or unsubstituted cycloalkyl group, or a substituted or unsubstituted alkenyl group; (ii) X is a group of the formula: —$NR^4$— ($R^4$ is a hydrogen atom, or a substituted or unsubstituted alkyl group), and $R^3$ is the same as defined above, or $R^4$ and $R^3$ may combine together with the nitrogen atom to which they bond to form a substituted or unsubstituted nitrogen-containing heterocyclic group, or a pharmaceutically acceptable salt thereof.

The terms used in the present specification are explained below.

The "substituted phenyl", the "substituted naphthyl", the "substituted furyl", the "substituted pyridyl" and the "substituted thienyl" have one or more substituents, and the substituent is, for example, a halogen atom, a $C_1$–$C_4$ alkyl group, a $C_2$–$C_4$ alkenyl group, a $C_1$–$C_4$ alkoxy group, a hydroxy group, a nitro group, a cyano group, a trifluoromethyl group, a mercapto group, —$S(O)_n(C_1$–$C_4$ alkyl) group, a carboxyl group, an ester group, an unsubstituted or substituted amino group, an unsubstituted or substituted amido group, an unsubstituted or substituted phenyl group, an unsubstituted or substituted phenyloxy group, etc. (in the above formula, n is 0, 1 or 2, hereinafter, the same).

The "aralkyl group" is, for example, an aralkyl group having 13 carbon atoms or less, and the aryl moiety thereof may be an aryl group having 10 carbon atoms or less such as phenyl, naphthyl, etc., and the alkyl moiety of the aralkyl group is, for example, an alkyl group having 1 to 3 carbon atoms such as methyl, ethyl, propyl, etc. The representative aralkyl group is, for example, benzyl group.

The "substituted aralkyl group" may have one or more substituents at the aryl moiety and/or the alkyl moiety, and the substituent is, for example, a halogen atom, a $C_1$–$C_4$ haloalkyl group, a $C_1$–$C_4$ alkyl group, a $C_2$–$C_4$ alkenyl group, a $C_1$–$C_4$ alkoxy group, a hydroxy group, a nitro group, a mercapto group, —$S(O)_n(C_1$–$C_4$ alkyl) group, a carboxyl group, an ester group, an unsubstituted or substituted amino group, an unsubstituted or substituted amido group, a substituted phenyloxy group, etc.

The "5- to 6-membered aromatic heterocyclic group" is, for example, a 5- to 6-membered aromatic heterocyclic group consisting of one heteroatom selected from an oxygen atom, a sulfur atom, a nitrogen atom, etc., and carbon atoms, such as 2-furyl, 3-furyl, 2-thienyl, 3-thienyl, 2-pyrrolyl, 3-pyrrolyl, 2-pyridyl, 3-pyridyl, 4-pyridyl, etc.

The "substituted 5- to 6-membered aromatic heterocyclic group" has one or more substituents, and the substituent is, for example, a halogen atom, a $C_1$–$C_4$ alkyl group, a $C_2$–$C_4$ alkenyl group, a $C_1$–$C_4$ alkoxy group, a hydroxy group, a mercapto group, —$S(O)_n(C_1$–$C_4$ alkyl) group, a carboxyl group, an ester group, an unsubstituted or substituted amino group, an unsubstituted or substituted amido group, an unsubstituted or substituted phenyloxy, etc.

The "cycloalkyl" is a 3- to 8-membered saturated hydrocarbons having a cyclic structure, such as cyclopropyl cyclohexyl, etc. The "substituted cycloalkyl group" has one or more substituents, and the substituent is, for example, a halogen atom, a $C_1$–$C_4$ alkyl group, a $C_1$–$C_4$ alkoxy group, a hydroxy group, a mercapto group, —$S(O)_n(C_1$–$C_4$ alkyl) group, an unsubstituted or substituted amino group, an unsubstituted or substituted amido group, etc.

The "alkyl" includes as a group per se or as a part of other substituents, and is a lower alkyl group unless defined otherwise, and the lower alkyl group is, for example, a straight chain or branched chain saturated hydrocarbon group having 1 to 6 carbon atoms, for example, a straight chain or branched chain group such as methyl, ethyl, n-propyl, isopropyl, n-butyl, t-butyl, isobutyl, sec-butyl, n-pentyl, n-hexyl, and includes also a higher analogues thereof such as 2-methylpentyl, and isomers of these groups.

The "substituted alkyl" has one-or more substituents, and the substituent is, for example, a halogen atom, a $C_1$–$C_4$ alkoxy group, a hydroxy group, an ester group, a carboxyl group, a mercapto group, —$S(O)_n(C_1$–$C_4$ alkyl) group, an unsubstituted or substituted amino group, an unsubstituted or substituted amido group, an unsubstituted or substituted furyl group, an unsubstituted or substituted thienyl group, an unsubstituted or substituted pyridyl group, etc., more specifically, (2-furyl)methyl, (3-furyl)-methyl, (2-thienyl) methyl, (3-thienyl)methyl, (2-pyridyl)-methyl, (3-pyridyl) methyl, (4-pyridyl)methyl, 1-ethoxyethyl, 2-ethoxyethyl, 1-hydroxyethyl, 2-hydoxyethyl, 1-hydroxypentyl, 2-hydroxypentyl, 3-hydroxypentyl, 4-hydroxypenyl, 5-hydroxypentyl, 1-dimethylamioethyl, 2-dimethylaminoethyl, 1-diethylaminoethyl, 2-diethylaminoethyl, 1-diisopropylaminoethyl, 2-diisopropylaminoethyl, 1-dimethylaminopropyl, 2-dimethylaminopropyl, 3-dimethylaminopropyl, ethoxycarbonylmethyl, 1-ethoxycarbonylethyl, 2-ethoxycarbonyl-ethyl etc.

The "alkenyl" is, for example, a straight chain or branched chain $C_2$–$C_6$ mono-unsaturated hydrocarbon group such as vinyl, 1-propenyl, allyl, isopropenyl, many butenyl isomers. The "substituted alkenyl" has one or more substituents, and the substituent is, for example, a halogen atom, a $C_1$–$C_4$ alkoxy group, a hydroxy group, an ester group, a mercapto group, —$S(O)_n(C_1$–$C_4$ alkyl) group, an unsubstituted or substituted amino group, an unsubstituted or substituted amido group, etc.

The "halogen atom" is chlorine atom, bromine atom, fluorine atom or iodine atom.

The "substituted amino group" is an amino group wherein one or both hydrogen atoms of the amino group are independently substituted, for example, by a halogen atom, a $C_1$–$C_4$ alkyl group, a $C_2$–$C_4$ alkenyl group, a $C_1$–$C_4$ alkoxy group, a hydroxy group, a mercapto group, or —$S(O)_n$ ($C_1$–$C_4$ alkyl) group, etc., and includes, for example, dimethylamino, diethylamino, diisopropylamino, etc.

The "heterocyclic group" may be an aromatic heterocyclic group or a saturated or unsaturated aliphatic heterocyclic group, for example, a 5- to 6-membered heterocyclic group consisting of 1 to 3 heteroatoms selected from a nitrogen atom, an oxygen atom and a sulfur atom, and carbon atoms, such as piperidinyl, piperazinyl, 2-oxopiperidinyl, 2-oxopiperazinyl, 2-oxopyrrolidinyl, 2-oxazepinyl, azepinyl, pyrrolyl, 4-piperidinyl, pyyrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, thiadiazolyl, furyl, tetrahydrofuryl, tetrahydropyranyl, thienyl, thiamorpholinyl, thiamorpholinyl sulfoxide, thiamorpholinyl-sulfone, oxadiazolyl, and triazolyl. The substituents of these groups may be 1 to 2 groups independently selected from a halogen atom, a $C_1$–$C_4$ alkyl group, a $C_2$–$C_4$ alkenyl group, a $C_1$–$C_4$ alkoxy group, a hydroxy group, a mercapto group, —S(O)$_n$($C_1$–$C_4$ alkyl) group, a carboxyl group, an ester group, a substituted or unsubstituted amino group, a substituted or unsubstituted amido group, etc.

The "nitrogen-containing heterocyclic group" is a saturated or unsaturated, 5- to 6-membered heterocyclic group consisting of 1 to 2 nitrogen atoms, 0 to 1 oxygen atom, 0 to 1 sulfur atom, and carbon atoms, for example, pyrrolidino, piperidino, morpholino, piperazino, etc. The substituent thereof may be 1 to 2 groups independently selected from a halogen atom, a substituted or unsubstituted $C_1$–$C_4$ alkyl group, a $C_2$–$C_4$ alkyenyl group, a $C_1$–$C_4$ alkoxy group, hydroxy group, a mercapto group, —S(O)$_n$($C_1$–$C_4$ alkyl) group, a carboxyl group, an ester group, a substituted or unsubstituted amino group, a substituted or unsubstituted amido group, etc.

The "nitrogen-containing aromatic cyclic group" is a 6-membered aromatic cyclic group consisting of 1 to 2 nitrogen atoms and carbon atoms, for example, pyridyl, pyridazyl, pyrimidyl, pyrazyl, etc. The substituents thereof may be 1 to 2 groups independently selected from a halogen atom, a $C_1$–$C_4$ alkyl group, a $C_2$–$C_4$ alkenyl group, a $C_1$–$C_4$ alkoxy group, a hydroxy group, a mercapto group, —S(O)$_n$ ($C_1$–$C_4$ alkyl) group, a carboxyl group, an ester group, an unsubstituted or substituted amino group, an unsubstituted or substituted amido group, etc.

The "ester group" means an esterified carboxyl group, and includes a ($C_1$–$C_6$ alkoxy)carbonyl group, an (aryl having not more than 10 carbon atoms)oxycarbonyl group, an aralkyloxycarbonyl group, etc. The representatives of the ester group are methoxycarbonyl, ethoxycarbonyl, phenoxycarbonyl, benzyloxycarbonyl, phenethyloxycarbonyl, etc.

The "amide" means an amidated carboxyl group, or an acylated amino group, for example, methyl carbonylamino, etc. The "acyl" includes an unsubstituted or substituted phenylcarbonyl group, an unsubstituted or substituted naphthylcarbonyl group, an unsubstituted or substituted aralkylcarbonyl group, an unsubstituted or substituted 5- to 6-membered aromatic heterocyclic carbonyl group, an unsubstituted or substituted ($C_1$–$C_6$ alkyl)carbonyl group, an unsubstituted or substituted ($C_2$–$C_6$ alkenyl)carbonyl group, etc.

The "substituted amido" is amidos wherein a hydrogen atom or both hydrogen atoms binding to the amido nitrogen atom are independently substituted by, for example, a halogen atom, a $C_1$–$C_4$ alkyl group, a $C_2$–$C_4$ alkenyl group, a $C_1$–$C_6$ alkoxy group, a hydroxy group, a mercapto group, —S(O)$_n$($C_1$–$C_4$ alkyl) group, etc.

The "pyridyl" means 2-pyridyl, 3-pyridyl, 4-pyridyl, and the preferred one is 2-pyridyl.

The preferable compounds as an active ingredient for LDL receptor gene expression promoters of the present invention have the following structures:

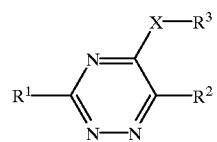

wherein $R^1$ is a substituted or unsubstituted nitrogen-containing aromatic cyclic group;

$R^2$ is a substituted or unsubstituted phenyl group;

X and $R^3$ are the following (i) or (ii):

(i) X is an oxygen atom or a sulfur atom, and $R^3$ is a substituted or unsubstituted phenyl group, a substituted or unsubstituted naphthyl group, a substituted or unsubstituted aralkyl group, a substituted or unsubstituted $C_1$–$C_6$ alkyl group, a substituted or unsubstituted cycloalkyl group, or a substituted or unsubstituted $C_1$–$C_6$ alkenyl group;

(ii) X is a group of the formula: —NR$^4$— ($R^4$ is a hydrogen atom, or a substituted or unsubstituted $C_1$–$C_6$ alkyl group), and $R^3$ is the same as defined above, or $R^4$ and $R^3$ may combine together with the nitrogen atom to which they bond to form a substituted or unsubstituted pyrrolidino group, a substituted or unsubstituted piperidino group, a substituted or unsubstituted morpholino group, or a substituted or unsubstituted piperazino group.

The more preferable compounds as an active ingredient for LDL receptor gene expression promoters of the present invention have the following structures:

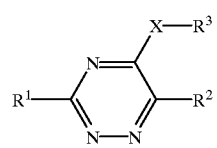

wherein $R^1$ is a substituted or unsubstituted pyridyl group;

$R^2$ is a substituted or unsubstituted phenyl group;

X and $R^3$ are the following (i) or (ii):

(i) X is an oxygen atom or a sulfur atom, and $R^3$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted $C_1$–$C_6$ alkyl group, a substituted or unsubstituted cycloalkyl group, or a substituted or unsubstituted $C_1$–$C_6$ alkenyl group;

(ii) X is a group of the formula: —NR$^4$— ($R^4$ is a hydrogen atom, or a substituted or unsubstituted $C_1$–$C_6$ alkyl group), and $R^3$ is the same as defined above, or $R^4$ and $R^3$ may combine together with the nitrogen atom to which they bond to form a substituted or unsubstituted pyrrolidino group, a substituted or unsubstituted piperidino group, a substituted or unsubstituted morpholino group, or a substituted or unsubstituted piperazino group.

The representative compounds being useful as an active ingredient of the present invention are listed below.

5-Allylamino-6-(2,4-dichlorophenyl)-3-(2-pyridyl)-1,2,4-triazine, 5-(t-Butylamino)-6-(2,4-dichlorophenyl)-3-(2-pyridyl)-1,2,4-triazine, 5-Benzylamino-6-(2,4-dichlorophenyl)-3-(2-pyridyl)-1,2,4-triazine, 6-(2,4-Dichlorophenyl)-5-cyclohexylamino-3-(2-pyridyl)-1,2,4-triazine, 5-Benzylamino-6-(4-methoxyphenyl)-3-(2-pyridyl)-1,2,4-triazine,
5-(4-Fluorobenzylamino)-6-(4-methoxyphenyl)-3-(2-pyridyl)-1,2,4-triazine,
5-(4-Chlorobenzylamino)-6-(4-methoxyphenyl)-3-(2-pyridyl)-1,2,4-triazine,
5-Benzylamino-3-(2-pyridyl)-6-(4-trifluoromethylphenyl)-1,2,4-triazine,
5-(4-Fluorobenzylamino)-3-(2-pyridyl)-6-(4-trifluoromethylphenyl)-1,2,4-triazine,
5-(4-Methoxybenzylamino)-3-(2-pyridyl)-6-(4-trifluoromethylphenyl)-1,2,4-triazine,
5-(3-Methoxybenzylamino)-3-(2-pyridyl)-6-(4-trifluoromethylphenyl)-1,2,4-triazine,
5-(2-Methoxybenzylamino)-3-(2-pyridyl)-6-(4-trifluoromethylphenyl)-1,2,4-triazine,
5-(4-Dimethylaminobenzylamino)-3-(2-pyridyl)-6-(4-trifluoromethylphenyl)-1,2,4-triazine,
5-(4-Nitrobenzylamino)-3-(2-pyridyl)-6-(4-trifluoromethylphenyl)-1,2,4-triazine,
3-(2-Pyridyl)-5-(4-trifluoromethylbenzylamino)-6-(4-trifluoromethylphenyl)-1,2,4-triazine,
3-(2-pyridyl)-5-(2-pyridylmethylamino)-6-(4-trifluoromethylphenyl)-1,2,4-triazine,
3-(2-Pyridyl)-5-(3-pyridylmethylamino)-6-(4-trifluoromethylphenyl)-1,2,4-triazine,
3-(2-Pyridyl)-5-(4-pyridylmethylamino)-6-(4-trifluoromethylphenyl)-1,2,4-triazine,
5-Pentylamino-3-(2-pyridyl)-6-(4-trifluoromethylphenyl)-1,2,4-triazine,
5-(2-Ethoxyethylamino)-3-(2-pyridyl)-6-(4-trifluoromethylphenyl)-1,2,4-triazine,
3-(2-Pyridyl)-5-(2-thienylmethylamino)-6-(4-trifluoromethylphenyl)-1,2,4-triazine,
1-Phenyl-2-(3-(2-pyridyl)-6-(4-trifluoromethylphenyl)-1,2,4-triazin-5-ylamino)-propane-1,3-diol,
2-(Benzyl-(3-(2-pyridyl)-6-(4-trifluoromethylphenyl)-1,2,4-triazin-5-yl) amino)-1-ethanol,
5-(2-Phenylethylamino)-3-(2-pyridyl)-6-(4-trifluoromethylphenyl)-1,2,4-triazine,
5-(N-Methylbenzylamino)-3-(2-pyridyl)-6-(4-trifluoromethylphenyl)-1,2,4-triazine,
5-(4-Methoxyphenylamino)-3-(2-pyridyl)-6-(4-trifluoromethylphenyl)-1,2,4-triazine,
5-(3-Dimethylaminopropylamino)-3-(2-pyridyl)-6-(4-trifluoromethylphenyl)-1,2,4-triazine,
5-Morpholino-3-(2-pyridyl)-6-(4-trifluoromethylphenyl)-1,2,4-triazine,
5-(3-(2-Pyridyl)-6-(4-trifluoromethylphenyl)-1,2,4-triazin-5-ylamino)-pentan-1-ol,
2-(4-(3-(2-Pyridyl)-6-(4-trifluoromethylphenyl)--1,2,4-triazin-5-yl)-piperazin-1-yl)-ethanol,
2-Ethyl-2-(3-(2-pyridyl)-6-(4-trifluoromethylphenyl)-1,2,4-triazin-5-ylamino)-propane-1,3-diol,
5-Benzylamino-6-(4-chlorophenyl)-3-(2-pyridyl)-1,2,4-triazine,
5-Benzylamino-6-(4-chlorophenyl)-3-(3-pyridyl)-1,2,4-triazine,
5-Benzylamino-6-(4-chlorophenyl)-3-(4-pyridyl)-1,2,4-triazine,
5-Ethoxy-3-(2-pyridyl) -6-(4-trifluoromethylphenyl)-1,2,4-triazine,
5-Methoxy-3-(2-pyridyl)-6-(4-trifluoromethylphenyl)-1,2,4-triazine,
5-Benzyloxy-3-(2-pyridyl)-6-(4-trifluoromethylphenyl)-1,2,4-triazine,
5-Benzylthio-3-(2-pyridyl)-6-(4-trifluoromethylphenyl)-1,2,4-triazine,
5-Ethylthio-3-(2-pyridyl)-6-(4-trifluoromethylphenyl)-1,2,4-triazine,
5-Furfurylthio-3-(2-pyridyl)-6-(4-trifluoromethylphenyl)-1,2,4-triazine,
5-Phenylthio-3-(2-pyridyl)-6-(4-trifluoromethylphenyl)-1,2,4-triazine,
5-(2-Dimethylaminoethylthio)-3-(2-pyridyl)-6-(4-trifluoromethylphenyl)-1,2,4-triazine,
5-(4-Chlorobenzylthio)-3-(2-pyridyl)-6-(4-trifluoromethylphenyl)-1,2,4-triazine,
5-(2-Fluorobenzylthio)-3-(2-pyridyl)-6-(4-trifluoromethylphenyl)-1,2,4-triazine,
5-(4-Methoxybenzylthio)-3-(2-pyridyl)-6-(4-trifluoromethylphenyl)-1,2,4-triazine,
5-(4-Methylbenzylthio)-3-(2-pyridyl)-6-(4-trifluoromethylphenyl)-1,2,4-triazine,
5-(2-Ethoxycarbonylethylthio)-3-(2-pyridyl)-6-(4-trifluoromethylphenyl)-1,2,4-triazine,
3-(2-Pyridyl)-5-(2-pyridylthio)-6-(4-trifluoromethylphenyl)-1,2,4-triazine,
5-Ethoxycarbonylmethylthio-3-(2-pyridyl)-6-(4-trifluoromethylphenyl)-1,2,4-triazine,
2-(3-(2-Pyridyl)-6-(4-trifluoromethylphenyl)-1,2,4-triazin-5-ylsulfanyl)-ethanol,
5-Allylthio-3-(2-pyridyl)-6-(4-trifluoromethylphenyl)-1,2,4-triazine,
5-Pentylthio-3-(2-pyridyl)-6-(4-trifluoromethylphenyl)-1,2,4-triazine,
5-Cyclohexylthio-3-(2-pyridyl)-6-(4-trifluoromethylphenyl)-1,2,4-triazine,
5-(2-Diisopropylaminoethylthio)-3-(2-pyridyl)-6-(4-trifluoromethylphenyl)-1,2,4-triazine,
5-(2-Acetylaminoethylthio)-3-(2-pyridyl)-6-(4-trifluoromethylphenyl)-1,2,4-triazine,
(3-(2-Pyridyl)-6-(4-trifluoromethylphenyl)-1,2,4-triazin-5-ylsulfanyl)acetic acid,
5-(2-Diethylaminoethylthio)-3-(2-pyridyl)-6-(4-trifluoromethylphenyl)-1,2,4-triazine,
5-(2-Phenylethylthio)-3-(2-pyridyl)-6-(4-trifluoromethylphenyl)-1,2,4-triazine,
5-(3-Phenylpropylthio)-3-(2-pyridyl)-6-(4-trifluoromethylphenyl)-1,2,4-triazine,
5-(3-Dimethylaminopropylthio)-3-(2-pyridyl)-6-(4-trifluoromethylphenyl)-1,2,4-triazine.

As mentioned above, the active ingredient of the present invention includes a pharmaceutically acceptable salt of the compound of the formula (I). The specific compound of the present invention may form a pharmaceutically acceptable salt by reacting with many inorganic acids, organic acids, or inorganic bases. An acid being usually used in order to form an acid addition salt is an inorganic acid such as hydrochloric acid, hydrobromic acid, sulfuric acid, phosphoric acid, etc. An organic carboxylic acid may be formic acid, acetic acid, fumaric acid, maleic acid, malic acid, tartaric acid, aparatic acid, glutamic acid, etc. A sulfonic acid may be methanesulfonic acid, benzenesulfonic acid, p-toluenesulfonic acid, hydroxybenzenesulfonic acid, dihydroxybenzenesulfonic acid, etc. The base-addition salt may be a salt derived from an inorganic base such as a hydroxide, carbonate or hydrogen carbonate of ammonium, alkali metal or alkaline earth metal. Specifically useful base for forming a base-addition salt may be sodium hydroxide, potassium hydroxide, ammonium hydroxide, potassium carbonate, sodium carbonate, sodium hydrogen carbonate, potassium hydrogen carbonate, calcium hydroxide, calcium carbonate, etc. Potassium and sodium are especially preferable.

Moreover, the above compounds or a salt thereof, which are an active ingredient of the present invention, may be in the form of either an anhydride, a hydrate (e.g., monohydrate, dihydrate) or a solvate.

The active ingredient of the present invention can be prepared by a method which is known in this field, for example, by a method disclosed in Liebigs Annalen der Chemie, p. 631, 1990, or in Heterocycles, vol. 26, p. 3259, 1987. That is, the 1,2,4-triazine derivative of the above formula (I) can be prepared by converting a 1,2,4-triazin-5-one derivative of the formula (II):

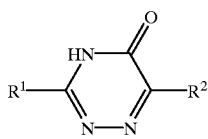
(II)

wherein $R^1$ is a substituted or unsubstituted phenyl group or a substituted or unsubstituted heterocylic group, $R^2$ is a substituted or unsubstituted phenyl group, a substituted or unsubstituted naphthyl group, a substituted or unsubstituted aralkyl group, a substituted or unsubstituted 5- to 6-membered aromatic heterocylic group, a substituted or unsubstituted alkyl group, or a substituted or unsubstituted alkenyl group, into a 5-chloro-1,2,4-triazine derivative of the formula (III):

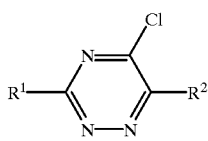
(III)

wherein $R^1$ and $R^2$ are the same as defined above, and followed by reacting the compound (III) with a corresponding amine or alkoxide or thiol.

Among the compounds (I), the 5-amino-1,2,4-triazine derivative and 5-oxy-1,2,4-triazine derivative will be prepared by a process as explained in more detail below.

The desired 5-chloro-1,2,4-triazine derivative (III) can be prepared by heating 1,2,4-triazin-5-one derivative (II) in the presence of thionyl chloride, and if necessary, in a suitable solvent. The 5-chloro-1,2,4-triazine derivative (III) thus obtained is then subjected to a reaction with an excess amount of a corresponding amine or alkoxide in a suitable solvent to give the desired 5-amino-1,2,4-triazine derivative and 5-oxy-1,2,4-triazine derivative inclusive in the compounds of the formula (I).

Among the compounds of the formula (I), the 5-thio-1,2,4-triazine derivative will be prepared by a process as explained in more detail below. That is, 5-chloro-1,2,4-triazine derivative (III) is reacted with an excess amount of a corresponding tiol in the presence of a basic substance in a suitable solvent to give the desired 5-thio-1,2,4-triazine derivative inclusive in the compounds (I).

Besides, during the step for preparing 1,2,4-triazine derivative (I), the produced 5-chloro-1,2,4-triazine derivative may not necessarily be isolated from the reaction mixture, but can be used in the subsequent reaction without isolation.

The solvent may be ethers such as tetrahydrofuran, dioxane, etc., halogenated hydrocarbons such as carbon tetrachloride, methylene chloride, etc., and dimethylformamide, but should not be limited thereto, and may be any solvent which does not disturb the reaction. The reaction is carried out at a temperature from 0 to 100° C., preferably at a temperature from 0 to 60° C., in the preparation of 5-thio-1,2,4-triazine derivative. In the preparation of other compounds (I) and the compound (III), the reaction is carried out at a temperature from 40 to 200° C., preferably at a temperature from 60 to 150° C.

The basic substance used in the preparation of 5-thio-1,2,4-triazine derivative of the formula (I) may be organic basic substances such as pyridine, triethylamine, dimethylaminopyridine, diisopropylethylamine, or inorganic basic substances such as sodium hydroxide, potassium hydroxide, sodium hydrogen carbonate, potassium carbonate, etc.

The compound (I) obtained in the present process may usually be separated and purified by chromatography, but also can be separated by a conventional other separation technique such as recrysallization.

The amine, alkoxide and thiol used in the preparation of the compoundn (I) may be commercially available ones, or can be prepared by a conventional method. For example, the alkoxide can be prepared by a method disclosed in Heterocycles, vol. 26, p. 3259, 1987. Besides, the thiol can be prepared by a method disclosed in Journal of Organometallic Chemistry, vol. 480, p. 177, 1994.

The 1,2,4-triazin-5-one derivative of the formula (II) may be prepared by a conventional method, for example, according to the method disclosed in U.S. Pat. No. 4,343,801. That is, the 1,2,4-triazin-5-one derivative of the above-mentioned formula (II) can be prepared by subjecting a ketocarboxylic acid derivative of the formula (IV):

$$R^2\text{—COCOOR}^5 \quad (IV)$$

wherein $R^2$ is the same as defined above, and $R^5$ is a hydrogen atom or a lower alkyl group, to a condensation reaction with an amidrazone derivative of the formula (V):

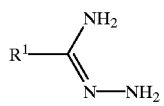
(V)

wherein $R^1$ is the same as defined above, to give a Schiff base of the formula (VI):

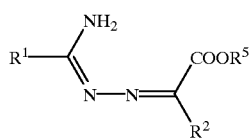
(VI)

wherein $R^1$, $R^2$ and $R^5$ are the same as defined above, then followed by cyclization reaction of the compound (VI).

The process for preparing the compound (II) is explained in more detail below. The ketocarboxylic acid (IV) and the amidrazone (V) are each used in equimolar amount, and condensed at room temperature in a solvent to give the desired Schiff base (VI), which is further heated in a solvent to give the desired compound (II). Besides, for preparing the 1,2,4-triazin-5-one derivative (II), it is not necessary to isolate the Schiff base (VI), and the desired compound (II) can directly be obtained by reacting the ketocarboxylic acid derivative (IV) and the amidrazone (V) with heating in a suitable solvent.

The solvent may be alcohols such as methanol, ethanol, etc., ethers such as tetrahydrofuran, dioxane, etc., halogenated hydrocarbons such as carbon tetrachloride, methylene chloride, etc., and dimethylformamide, etc., but should not be limited thereto, and may be any solvent which does not disturb the reaction. The reaction is usually carried out at room temperature when preparing the compound (VI), but when preparing the compound (II), the reaction is carried out at a temperature from 40 to 300° C., preferably at a temperature from 60 to 200° C.

The compound (II) obtained in this process can usually be separated or purified by chromatography, and also separated by a conventional separation technique such as recrsytallization.

The ketocarboxylic acid derivative (IV) and the amidrazone (V) may be commercially available ones, or can be prepared by a conventional method. For example, the keto acid can be prepared by the methods disclosed in Collection of Czechoslovak Chemical Communication, vol. 29, p. 97, 1964, Journal of Organic Chemistry, vol. 52, p. 50,26, 1987, Mecicinal Chemistry Research, vol. 4, p. 385, 1994, or the Literature of Saseho Technical High School, vol. 25, p. 119, 1988. The amidrazone may be prepared by the method disclosed in Chemical Reviews, vol. 70, p. 151, 1970.

The compound of the formula (I) or a salt thereof can be administered either orally or parenterally in the form of a pharmaceutical composition. That is, the compound (I) or a salt thereof can be administered in a conventional administration form, for example, in the form of tablets, capsules, syrups, suspensions, etc. for oral administration, or in the form of an injection form such as liquid preparations (e.g., solutions, emulsions, suspensions, etc.) for parenteral administration. The compound of the formula (I) of the present invention or a pharmaceutically acceptable salt thereof may also be administered by a rectal route in the form of a suppository. These preparations can be prepared by mixing the active compound with a conventional carrier, diluent, binder, stabilizer, etc. In the preparation of injection preparation, it can contain a pharmaceutically acceptable buffering agent, solubilizer, isotonic agent, etc.

The dosage and the administration frequency of the active compound (I) vary according to the conditions, ages, weights of the patients, or the administration forms, but the active compound (I) of the present invention is administered in a dose of about 1 to 2000 mg/day/adult, preferably in a dose of 5 to 1000 mg/day/adult, for the oral administration, and 0.1 to 500 mg/day/adult for the injection, once a day or in several times per day.

BEST MODE FOR CARRYING OUT THE INVENTION

The present invention is illustrated in more detail by the following Examples, but should not be construed to be limited to the Examples.

EXAMPLE 1

Preparation of 5-benzylamino-6-(2,4-dichlorophenyl)-3-(2-pyridyl)-1,2,4-triazine A mixture of 6-(2,4-dichlorophenyl)-3-(2-pyridyl)-1,2,4-triazin-5-one (5.00 g, 15.7 mmol) and thionyl chloride (50 ml) was heated under reflux for two hours. The mixture was allowed to cool to room temperature, and the solvent was removed by distillation under reduced pressure. To the residue were added tetrahydrofuran (50 ml), benzylamine (4.20 g, 39.2 mmol, 2.5 eq.), and the mixture was heated under reflux for two hours. The mixture was allowed to cool to room temperature, and water (150 ml) was added to the reaction mixture. The mixture was extracted with methylene chloride (600 ml), and washed with a 5% aqueous potassium hydrogen carbonate solution (150 ml), and further washed with a 5% brine (150 ml). The organic layer was dried over magnesium sulfate, filtered, and concentrated under reduced pressure. The resulting solid was purified by flash silica gel column chromatography (methylene chloride) to give the title compound as pale yellow crystals (3.64 g, 57%).

NMR (CDCl$_3$) 4.85 (br, 2H), 5.28 (br, 1H), 7.25–7.48 (m, 3H), 7.51 (s, 1H), 7.87 (t, J=7.58 Hz, 1H), 8.51 (d, J=7.58 Hz, 1H), 8.84 (d, J=3.96 Hz)

EXAMPLES 2–34

The compounds of Examples 2–34 as listed in Tables 1 to 5 were obtained in the same manner as in Example 1. In Table 1, the compound of Example 1 is also shown.

TABLE 1

| | Structure | NMR |
|---|---|---|
| Example 1 | [structure diagram] | (CDCl$_3$) δ: 4.85 (br, 2H), 5.28 (br, 1H), 7.25–7.40 (m, 3H), 7.51 (s, 1H), 7.87 (t, J = 7.58 Hz, 1H), 8.51 (d, J = 7.58 Hz, 1H), 8.84 (d, J = 3.96 Hz) |
| Example 2 | [structure diagram] | (CDCl$_3$) δ: 2.34 (br, 1H), 5.16–5.35 (m, 3H), 5.86–6.02 (m, 1H), 7.37–7.47 (m, 3H), 7.51 (d, J = 1.32 Hz, 1H), 7.87 (dt, J = 1.98 and 7.92 Hz, 1H)), 8.51 (dd, J = 0.99, 8.92 Hz, 1H), 8.83 (m, 1H) |

TABLE 1-continued
| Structure | NMR |
|---|---|
| Example 3 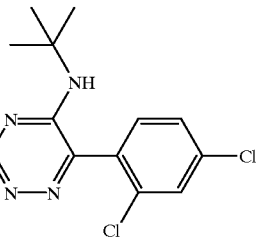 | (CDCl₃) δ: 1.55 (s, 9H), 4.80 (br, 1H), 7.30–7.52 (m, 3H), 7.55 (s, 1H), 7.86 (t, J = 7.59 Hz, 1H), 8.40 (d, J = 7.59 Hz, 1H), 8.86 (d, J = 3.96 Hz, 1H) |
| Example 4 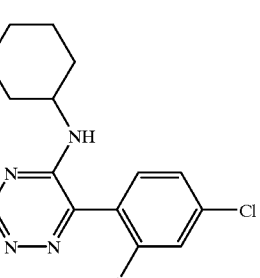 | (CDCl₃) δ: 1.10–1.32 (m, 3H), 1.32–1.57 (m, 2H), 1.57–1.90 (m, 3H), 1.90–2.20 (m, 2H), 4.19–4.36 (m, 1H), 4.75 (br, 1H), 7.38–7.55 (m, 3H), 7.56 (d, J = 1.32 Hz, 1H), 7.88 (t, J = 7.92 Hz, 1H), 8.47 (d, J = 7.92 Hz, 1H), 8.86 (d, J = 4.62 Hz, 1H) |
| Example 5 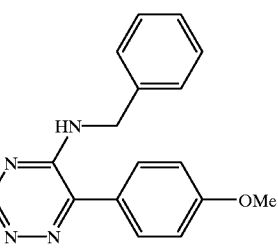 | (CDCl₃) δ: 3.84 (s, 3H), 4.85 (d, J = 5.61 Hz, 2H), 5.88 (br t, J = 5.61 Hz, 1H), 7.02 (d, J = 8.58 Hz, 2H), 7.19–7.42 (m, 6H), 7.66 (d, J = 8.58 Hz, 2H), 7.78–7.90 (m, 1H), 8.45–8.52 (m, 1H), 8.78–8.84 (m, 1H) |
| Example 6 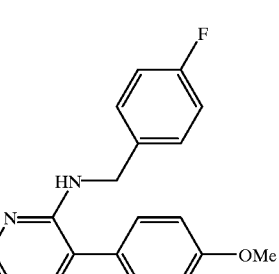 | (CDCl₃) δ: 3.85 (s, 3H), 4.82 (d, J = 5.28 Hz, 2H), 5.86 (br t, J = 5.28 Hz, 1H), 6.98–7.08 (m, 4H), 7.29–7.46 (m, 3H), 7.66 (d, J = 8.91 Hz, 2H), 7.86 (dt, J = 7.92 & 1.65 Hz, 1H), 8.50 (d, J = 7.92 Hz, 1H), 8.84 (d, J = 4.95 Hz, 1H) |
| Example 7 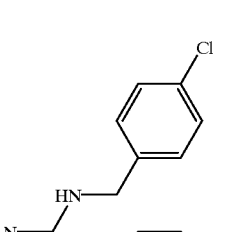 | (CDCl₃) δ: 3.85 (s, 3H), 4.65 (d, J = 5.61 Hz, 2H), 5.91 (br t, J = 5.61 Hz, 1H), 7.02 (d, 1H, J = 8.91 Hz, 2H), 7.30 (s, 4H), 7.38–7.46 (m, 1H), 7.65 (d, J = 8.58 Hz, 2H), 7.85 (dt, J = 7.92 & 1.65 Hz, 1H), 8.48 (d, J = 7.92 Hz, 1H), 8.83 (d, J = 3.96 Hz, 1H) |

TABLE 1-continued

| Structure | NMR |
|---|---|
| Example 8 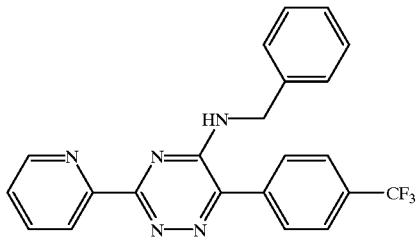 | (CDCl$_3$) δ: 4.88 (d, J = 5.61 Hz, 2H), 5.84 (br t, J = 5.61 Hz, 1H), 7.27–7.38 (m, 5H), 7.41–7.46 (m, 1H), 7.77 (d, J = 8.25 Hz, 2H), 7.86 (d, J = 8.25 Hz, 2H), 7.82–7.91 (m, 1H), 8.50 (d, J = 7.92 Hz, 1H), 8.82–8.86 (m, 1H) |

TABLE 2

| Structure | NMR |
|---|---|
| Example 9 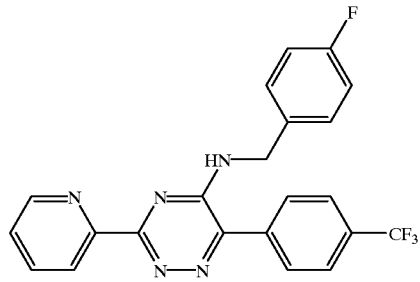 | (CDCl$_3$) δ: 4.83 (d, J = 5.28 Hz, 2H), 5.78 (br, 1H), 7.02 (t, J = 8.58 Hz, 2H), 7.34 (dd, J = 5.28, 8.25 Hz, 2H), 7.45 (dd, J = 4.29, 7.59 Hz, 1H), 7.76–7.91 (m, 5H), 8.51 (d, J = 7.92 Hz, 1H), 8.84 (d, J = 4.62 Hz, 1H) |
| Example 10 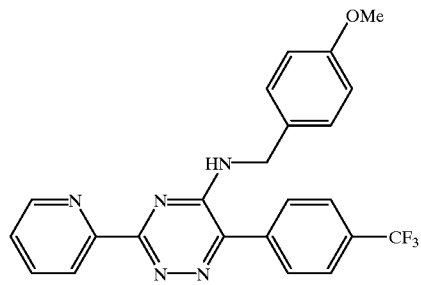 | (CDCl$_3$) δ: 3.78 (s, 3H), 4.79 (d, J = 5.28 Hz, 2H), 5.71 (br, 1H), 6.86 (t, J = 7.92 Hz, 2H), 7.27 (d, J = 8.25 Hz, 2H), 7.44 (dd, J = 4.95, 7.59 Hz, 1H), 7.74–7.90 (m, 5H), 8.53 (d, J = 7.92 Hz, 1H), 8.84 (d, J = 4.95 Hz, 1H) |
| Example 11 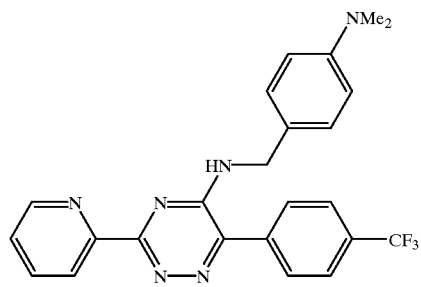 | (CDCl$_3$) δ: 2.93 (s, 6H), 4.75 (d, J = 4.95 Hz, 2H), 5.67 (br t, J = 4.95 Hz, 1H), 6.68 (d, J = 8.91 Hz, 2H), 7.22 (d, J = 8.57 Hz, 2H), 7.44 (dd, J = 7.59, 4.62 Hz, 1H), 7.75 (d, J = 8.25 Hz, 2H), 7.84 (d, J = 8.25 Hz, 2H), 7.88 (t, J = 7.92 Hz, 1H), 8.55 (d, J = 7.92 Hz, 1H), 8.86 (d, J = 4.62 Hz, 1H) |
| Example 12 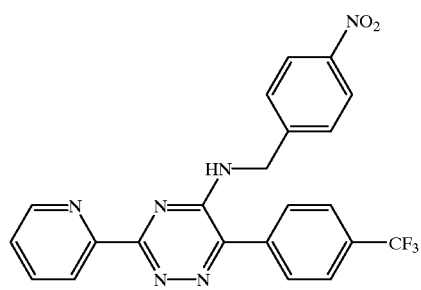 | (CDCl$_3$) δ: 4.99 (d, J = 5.61 Hz, 2H), 6.77 (br t, J = 5.61 Hz, 1H), 7.43 (dd, J = 7.59, 4.62 Hz, 1H), 7.59 (d, J = 8.91 Hz, 2H), 7.66 (d, J = 8.58 Hz, 2H), 7.80 (d, 8.91 Hz, 2H), 7.80–7.88 (m, 1H), 8.15 (d, J = 8.57 Hz, 2H), 8.35 (d, J = 7.92 Hz, 1H), 8.73 (d, J = 4.95 Hz) |

TABLE 2-continued

| | Structure | NMR |
|---|---|---|
| Example 13 | 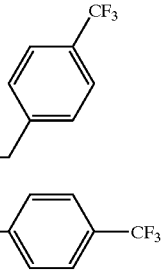 | (CDCl₃) δ: 4.94 (d, J = 5.93 Hz, 2H), 6.40 (t, J = 5.93 Hz, 1H), 7.39–7.49 (m, 1H), 7.51 (d, J = 8.58 Hz, 2H), 7.58 (d, J = 8.58 Hz, 2H), 7.70 (d, J = 8.57 Hz, 2H), 7.81 (d, J = 8.57 Hz, 2H), 7.86 (dt, J = 7.92, 1.98 Hz, 1H), 8.40 (d, J = 7.92 Hz, 1H), 8.76 (d, J = 4.62 Hz) |
| Example 14 | 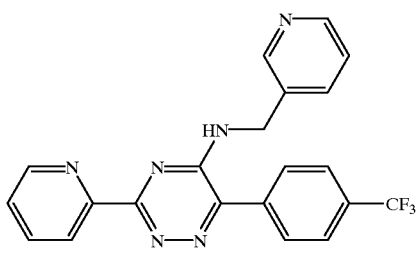 | (CDCl₃) δ: 4.82 (d, J = 5.61 Hz, 2H), 6.24 (br t, J = 5.61 Hz, 1H), 7.18 (dd, J = 7.59, 4.95 Hx, 1H), 7.36 (dd, J = 6.26, 4.95 Hz, 1H), 7.65 (d, J = 8.25 Hz, 2H), 7.65–7.72 (m, 1H), 7.75 (d, J = 8.25 Hz, m 2H), 7.80 (dt, J = 7.92, 1.65 Hz, 1H), 8.38 (d, J = 7.92 Hz, 1H), 8.44 (dd, J = 4.95, 1.65 Hz, 1H), 8.58 (d, J = 1.98, 1H), 8.73 (d, J = 3.96 Hz) |
| Example 15 | 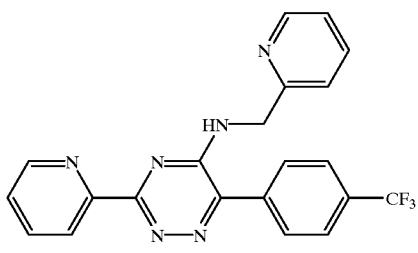 | (CDCl₃) δ: 4.98 (d, J = 4.29 Hz, 2H), 7.23 (dt, J = 4.95, 7.25 Hz, 1H), 7.36 (d, J = 7.59 Hz, 1H), 7.40–7.49 (m, 1H), 7.50 (t, J = 4.29 Hz, 1H), 7.70 (dt, J = 7.59, 1.92 Hz, 1H), 7.86 (d, J = 8.25 Hz, 2H), 7.90 (dt, J = 7.92, 1.65 Hz), 8.03 (d, J = 8.25 Hz, 2H), 8.50 (d, J = 4.95 Hz, 8.59 (d, J = 7.92 Hz, 1H), 8.89 (d, J = 4.62 Hz) |
| Example 16 | 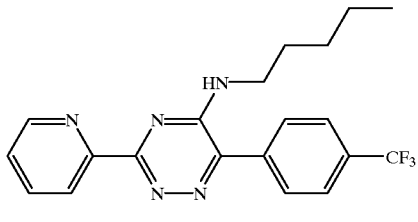 | (CDCl₃) δ: 0.90 (t, J = 6.93 Hz, 3H), 1.36–1.38 (m, 4H), 1.63–1.66 (m, 2H), 3.66 (q, J = 7.26 Hz, 2H), 5.44 (br, 1H), 7.43 (ddd, J = 0.99, 4.95, 7.59 Hz, 1H), 7.80–7.91 (m, 5H), 8.51 (d, J = 7.92 Hz, 1H), 8.85 (d, J = 3.96 Hz, 1H) |

TABLE 3

| | Structure | NMR |
|---|---|---|
| Example 17 | 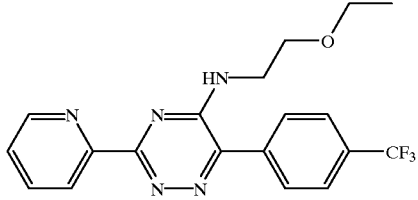 | (CDCl₃) δ: 1.15 (t, J = 6.93 Hz, 3H), 3.51 (q, J = 6.93 Hz, 2H), 3.65 (t, J = 5.28 Hz, 2H), 3.88 (q, J = 5.28 Hz, 2H), 6.01 (br, 1H), 7.43 (ddd, J = 1.32, 4.62, 7.59 Hz, 1H), 7.80–7.92 (m, 5H), 8.54 (d, J = 7.92 Hz, 1H), 8.85 (d, J = 3.96 Hz, 1H) |

TABLE 3-continued

| Structure | NMR |
|---|---|

Example 18 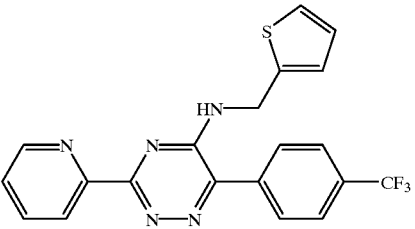

(CDCl₃) δ: 5.04 (d, J = 5.61 Hz, 2H), 6.06 (br, 1H), 6.93–6.96 (m, 1H), 7.05–7.06 (m, 1H), 7.44 (dd, J = 4.62, 7.59 Hz, 1H), 7.72–7.91 (m, 5H), 8.55 (d, J = 7.92 Hz, 1H), 8.82 (d, J = 4.62 Hz, 1H)

Example 19 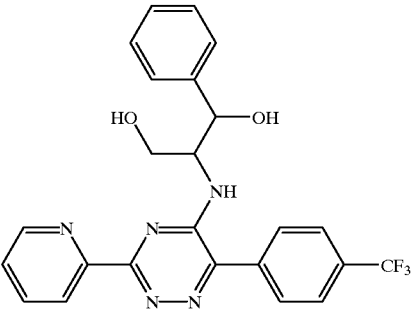

(CDCl₃) δ: 2.93 (s, 6H), 4.75 (d, J = 4.95 Hz, 2H), 5.67 (br t, J = 4.95 Hz, 1H), 6.68 (d, J = 8.91 Hz, 2H), 7.22 (d, J = 8.57 Hz, 2H), 7.44 (dd, J = 7.59, 4.62 Hz, 1H), 7.75 (d, J = 8.25 Hz, 2H), 7.84 (d, J = 8.25 Hz, 2H), 7.88 (t, J = 7.92 H, 1H), 8.55 (d, J = 7.92 Hz, 1H), 8.86 (d, J = 4.62 Hz, 1H)

Example 20 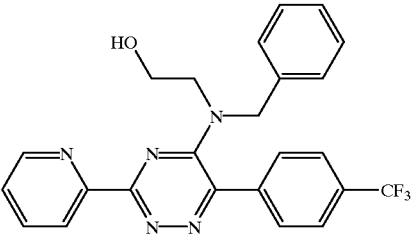

(CDCl₃) δ: 3.70–3.90 (m, 4H), 4.40 (s, 2H), 5.60–6.30 (br, 1H), 6.80–6.95 (2H), 7.15–7.25 (m, 4H), 7.40–7.50 (m, 1H), 7.61 (d, J = 8.58 Hz, 2H), 7.72 (d, J = 8.25, 2H), 7.89 (dt, J = 7.92, 1.65 Hz, 1H), 8.64 (d, J = 7.92 Hz, 1H), 8.78 (d, J = 4.62, 1H)

Example 21 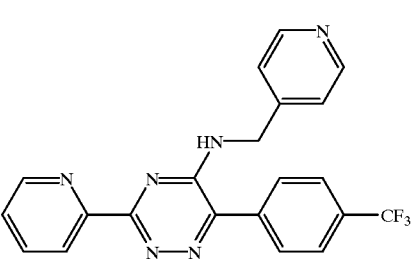

(CDCl₃) δ: 4.89 (d, J = 5.94 Hz, 2H), 6.64 (t, J = 5.94 Hz, 1H), 7.28 (d, J = 5.94 Hz, 2H), 7.30–7.50 (m, 1H), 7.70 (d, 7.91 Hz, 2H), 7.82 (d, J = 7.91 Hz, 2H), 7.79–7.88 (m, 1H), 8.33 (d, J = 7.92 Hz, 1H), 8.51 (d, J = 5.94 Hz, 2H), 8.75 (d, J = 4.94 Hz, 1H).

Example 22 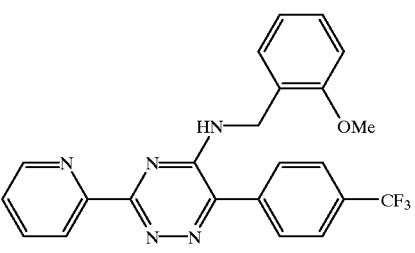

(CDCl₃) δ: 3.78 (s, 3H), 4.85 (d, J = 5.61 Hz, 2H), 6.26 (br, 1H), 6.88–6.95 (m, 2H), 7.29 (t, J = 7.92 Hz, 1H), 7.36 (d, J = 7.58 Hz, 1H), 7.44 (dd, J = 4.62, 7.59 Hz, 1H), 7.77–7.91 (m, 5H), 8.53 (d, J = 7.92 Hz, 1H), 8.87 (d, J = 3.96 Hz, 1H)

TABLE 3-continued

| | Structure | NMR |
|---|---|---|
| Example 23 | 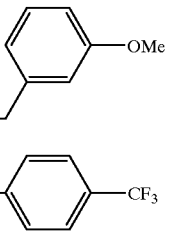 | (CDCl$_3$) δ: 3.76 (s, 3H), 4.84 (d, J = 5.28 Hz, 2H), 5.84 (br, 1H), 6.83 (dd, J = 1.65, 8.25 Hz, 1H), 6.91–6.93 (m, 2H), 7.26 (t, J = 8.25 Hz, 1H), 7.43 (dd, J = 4.95, 6.27 Hz, 1H), 7.75–7.89 (m, 5H), 8.51 (d, J = 7.92 Hz, 1H), 8.83 (d, J = 4.62 Hz, 1H) |
| Example 24 | 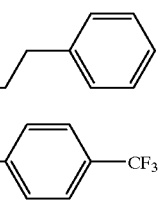 | (CDCl$_3$) δ: 2.99 (t, J = 6.60 Hz, 3H), 3.94 (q, J = 6.60 Hz, 2H), 5.43 (br, 1H), 7.16–7.30 (m, 5H), 7.43 (dd, J = 4.62, 7.59 Hz, 1H), 7.61 (d, J = 8.25 Hz, 2H), 7.68 (d, J = 8.57 Hz, 2H), 7.88 (t, J = 7.92 Hz, 1H), 8.52 (d, J = 7.92 Hz, 1H), 8.85 (d, J = 3.96 Hz, 1H) |

TABLE 4

| | Structure | NMR |
|---|---|---|
| Example 25 | 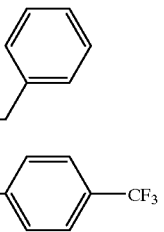 | (CDCl$_3$) δ: 2.88 (s, 3H), 4.85 (s, 2H), 7.18–7.31 (m, 5H), 7.42 (dd, J = 4.62, 7.59 Hz, 1H), 7.70 (d, J = 8.25 Hz, 2H), 7.80 (d, J = 8.58 Hz, 2H), 7.86 (t, J = 7.92 Hz, 1H), 8.52 (d, J = 7.92 Hz, 1H), 8.85 (d, J = 4.95 Hz, 1H) |
| Example 26 | 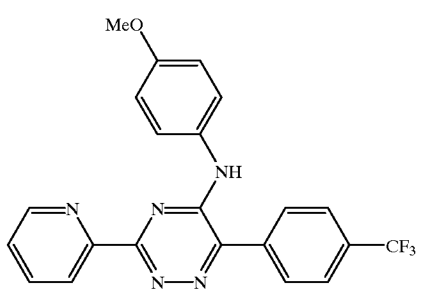 | (CDCl$_3$) δ: 3.79 (s, 3H), 6.90 (d, J = 8.91 Hz, 2H), 7.41 (dd, J = 5.61, 6.60 Hz, 1H), 7.50 (br, 1H), 7.69 (d, J = 8.91 Hz, 2H), 7.75 (d, J = 8.25 Hz, 2H), 7.82–7.89 (m, 3H), 8.40 (d, J = 7.92 Hz, 1H), 8.77 (d, J = 3.96 Hz, 1H) |
| Example 27 | 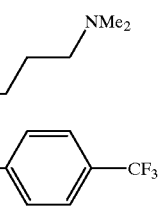 | (CDCl$_3$) δ: 1.70–1.76 (m, 2H), 1.86 (s, 6H), 2.40–2.44 (m, 2H), 3.74–3.80 (m, 2H), 7.41 (dd, J = 4.95, 6.60 Hz, 1H), 7.77–7.89 (m, 5H), 8.54 (d, J = 7.92 Hz, 1H), 8.78 (br, 1H), 8.84 (m, 1H) |

TABLE 4-continued

| | Structure | NMR |
|---|---|---|
| Example 28 | 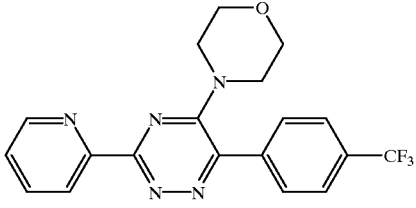 | (CDCl$_3$) δ: 3.56–3.61 (m, 2H), 3.68–3.72 (m, 2H), 7.42 (dd, J = 4.62, 7.59 Hz, 1H), 7.78 (d, J = 7.92 Hz, 2H), 7.89 (t, J = 7.92 Hz, 1H), 7.95 (d, J = 8.25 Hz, 2H), 8.56 (d, J = 7.92 Hz, 1H), 8.85 (d, J = 3.96 Hz, 1H) |
| Example 29 | 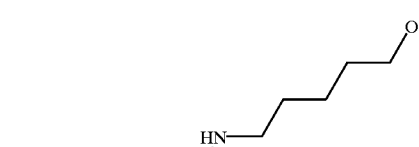 | (CDCl$_3$) δ: 4.89 (d, J = 5.94 Hz, 2H), 6.64 (t, J = 5.94 Hz, 1H), 7.28 (d, J = 5.94 Hz, 2H), 7.30–7.50 (m, 1H), 7.70 (d, J = 7.91 Hz, 2H), 7.82 (d, J = 7.91 Hz, 2H), 7.79–7.88 (m, 1H), 8.33 (d, J = 7.92 Hz, 1H), 8.51 (d, J = 5.94 Hz, 2H), 8.75 (d, J = 4.94 Hz, 1H) |
| Example 30 | 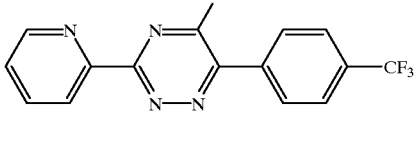 | (CDCl$_3$) δ: 2.25–2.59 (m, 7H), 3.59 . 3.63 (m, 6H), 7.42 (dd, J = 3.63, 6.27 Hz, 1H), 7.78 (d, J = 8.58 Hz, 2H), 7.85–7.95 (m, 3H), 8.56 (d, J = 8.25 Hz, 1H), 8.85 (d, J = 5.61 Hz, 1H) |
| Example 31 | 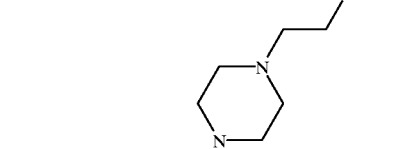 | (CDCl$_3$) δ: 0.93 (t, J = 7.59 Hz, 3H), 1.85 (q, J = 7.59 Hz, 2H), 3.76 (d, J = 11.8 Hz, 2H), 4.04 (d, J = 11.87 Hz, 2H), 5.37 (br, 2H), 6.23 (br, 1H), 7.38 (dd, J = 4.95, 7.58 Hz, 1H), 7.68–7.83 (m, 5H), 8.44 (d, J = 7.91 Hz, 1H), 8.67 (d, J = 4.65 Hz, 1H) |
| Example 32 | 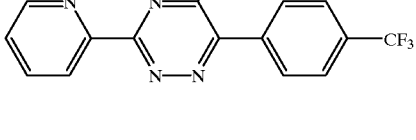 | (CDCl$_3$) δ: 4.86 (d, J = 5.28 Hz, 2H), 5.88 (br, 1H), 7.30–7.47 (m, 8H), 7.65 (d, J = 8.25 Hz, 2H), 7.85 (t, J = 7.59 Hz, 1H), 8.49 (d, J = 8.59 Hz, 1H), 8.81 (s, 1H) |

TABLE 5

| Structure | NMR |
|---|---|
| Example 33 [structure: 3-(3-pyridyl)-5-(benzylamino)-6-(4-chlorophenyl)-1,2,4-triazine] | (CDCl₃) δ: 4.81 (d, J = 5.60 Hz, 2H), 5.94 (br, 1H), 7.31–7.36 (m, 5H), 7.42 (dd, J = 4.95, 7.92 Hz, 1H), 7.50 (d, J = 8.58 Hz, 2H), 7.66 (d, J = 8.58 Hz, 2H), 8.70–8.77 (m, 2H), 9.64 (d, J = 1.32 Hz, 1H) |
| Example 34 [structure: 3-(4-pyridyl)-5-(benzylamino)-6-(4-chlorophenyl)-1,2,4-triazine] | (CDCl₃) δ: 3.79 (s, 3H), 6.90 (d, J = 8.91 Hz, 2H), 7.41 (dd, J = 5.61, 6.60 Hz, 1H), 7.50 (br, 1H), 7.69 (d, J = 8.91 Hz, 2H), 7.75 (d, J = 8.25 Hz, 2H), 7.82–7.89 (m, 3H), 8.40 (d, J = 7.92 Hz, 1H), 8.77 (d, J = 3.96 Hz, 1H) |

EXAMPLE 35

Preparation of 5-ethoxy-3-(2-pyridyl)-6-(4-trifluoromethylphenyl)-1,2,4-triazine A mixture of 3-(2-pyridyl)-6-(4-trifluoromethylphenyl)-1,2,4-triazin-5-one (10.00 g, 31.4 mmol) and thionyl chloride (100 ml) was heated under reflux for two hours. The mixture was allowed to cool to room temperature, and the solvent was distilled off. To the residue were added tetrahydrofuran (100 ml) and sodium ethoxide (10.69 g, 157 mmol, 15.0 eq.), and the mixture was heated under reflux for two hours. The mixture was allowed to cool to room temperature, and water (300 ml) was added to the reaction mixture. The mixture was extracted with methylene chloride (300 ml), and washed with water (200 ml), and then washed with 5% brine (200 ml). The organic layer was dried over magnesium sulfate, filtered, and concentrated under reduced pressure to remove the solvent. The resulting solid was purified by flash silica gel column chromatography (ethyl acetate-hexane) to give the title compound (7.57 g, 70%) as pale yellow prisms.

NMR (CDCl₃) 1.55 (t, J=7.26 Hz, 3H), 4.81 (q, J=7.26 Hz, 2H), 7.48 (dd, J=3.63, 7.59 Hz, 1H), 7.79 (d, J=8.25 Hz, 2H), 7.92 (td, J=7.92, 1.65 Hz, 1H), 8.34 (d, J=8.25 Hz, 2H), 8.61 (d, J=8.24 Hz, 1H), 8.90 (d, J=3.95 Hz, 1H)

EXAMPLES 36–37

The compounds of Examples 36–37 as listed in Table 6 were obtained in a similar manner as in Example 35. In Table 6, the compound of Example 35 is also shown.

TABLE 6

| Structure | NMR |
|---|---|
| Example 35 [structure: 5-ethoxy-3-(2-pyridyl)-6-(4-trifluoromethylphenyl)-1,2,4-triazine] | (CDCl₃) δ: 1.55 (t, J = 7.26 Hz, 3H), 4.81 (q, J = 7.26 Hz, 2H), 7.48 (dd, J = 3.63, 7.59 Hz, 1H), 7.79 (d, J = 8.25 Hz, 2H), 7.92 (td, J = 7.92, 1.65 Hz, 1H), 8.34 (d, J = 8.25 Hz, 2H), 8.61 (d, J = 8.24 Hz, 1H), 8.90 (d, J = 3.95 Hz, 1H) |
| Example 36 [structure: 5-methoxy-3-(2-pyridyl)-6-(4-trifluoromethylphenyl)-1,2,4-triazine] | (CDCl₃) δ: 4.32 (s, 3H), 7.49 (dd, J = 5.61, 6.60 Hz, 1H), 7.79 (d, J = 8.58 Hz, 2H), 7.93 (t, J = 7.59 Hz, 1H), 8.32 (d, J = 7.92 Hz, 2H), 8.63 (d, J = 7.92 Hz, 1H), 8.89 (m, 1H) |

TABLE 6-continued

| Structure | NMR |
|---|---|
| Example 37 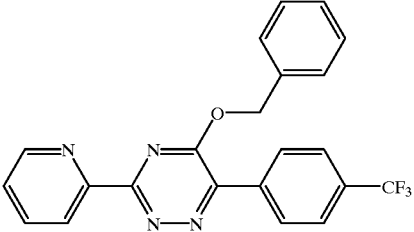 | (CDCl$_3$) δ: 5.78 (s, 2H), 7.39–7.54 (m, 6H), 7.75 (d, J = 8.25 Hz, 2H), 7.94 (t, J = 7.59 Hz, 1H), 8.33 (d, J = 8.25 Hz, 2H), 8.63 (d, J = 8.24 Hz, 1H), 8.92 (d, J = 5.60 Hz, 1H) |

EXAMPLE 38
Preparation of 5-benzylthio-3-(2-pyridyl)-6-(4-trifluoromethylphenyl)-1,2,4-triazine:

A mixture of 3-(2-pyridyl)-6-(4-trifluoromethylphenyl)-1,2,4-triazin-5-one (200 mg, 0.63 mmol) and thionyl chloride (5 ml) was heated under reflux for 30 minutes. The mixture was allowed to cool to room temperature, and the solvent was distilled off. To the residue were added tetrahydrofuran (4 ml), phenyl methanethiol (195 mg, 1.57 mmol, 2.5 eq.), and triethylamine (159 mg, 1.57 mmol, 2.5 eq.), and the mixture was stirred at room temperature for one hour. To the reaction mixture was added methylene chloride (50 ml), and the mixture was washed with water (20 ml), a saturated aqueous sodium hydrogen carbonate solution (20 ml) and a saturated brine (20 ml). The organic layer was dried over magnesium sulfate, filtered, and concentrated under reduced pressure to remove the solvent. The resulting solid was purified by flash silica gel column chromatography (chloroform) to give the title compound (248 mg, 93%) as pale yellow crystals.

NMR (CDCl$_3$) 4.62 (s, 2H), 7.27–7.32 (m, 3H), 7.45–7.53 (m, 3H), 7.79 (d, J=7.92 Hz, 2H), 7.90–7.99 (m, 3H), 8.58 (d, J=8.25 Hz, 1H), 8.90–8.93 (m, 1H)

EXAMPLES 39–60

The compounds of Examples 39–60 as listed in Tables 7–9 were obtained in a similar manner as in Example 38. In Table 7, the compound of Example 38 is also shown.

TABLE 7

| Structure | NMR |
|---|---|
| Example 38 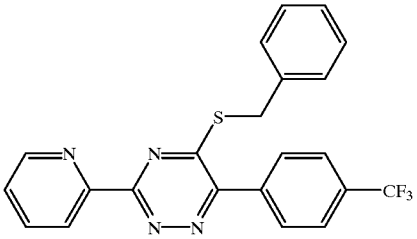 | (CDCl$_3$) δ: 4.62 (s, 2H), 7.27–7.32 (m, 3H), 7.45–7.53 (m, 3H), 7.79 (d, J = 7.92 Hz, 2H), 7.90–7.99 (m, 3H), 8.58 (d, J = 8.25 Hz, 1H), 8.90–8.93 (m, 1H) |
| Example 39 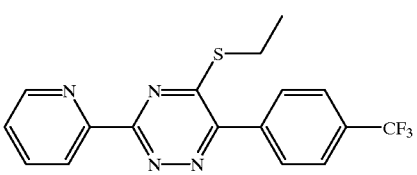 | (CDCl$_3$) δ: 2.34 (br, 1H), 5.16–5.35 (m, 3H), 5.86–6.02 (m, 1H), 7.37–7.47 (m, 3H), 7.51 (d, J = 1.32 Hz, 1H), 7.87 (dt, J = 1.98 and 7.92 Hz, 1H)), 8.51 (dd, J = 0.99, 7.92 Hz, 1H), 8.83 (m, 1H) |
| Example 40 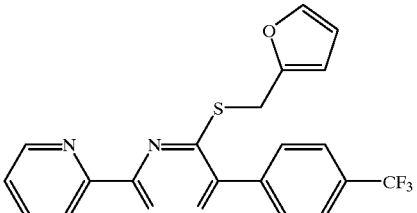 | (CDCl$_3$) δ: 4.67 (s, 2H), 6.28 (dd, J = 1.98, 3.30 Hz, 1H), 6.51 (d, J = 2.97 Hz, 1H), 7.33–7.34 (m, 1H), 7.51 (dd, J = 4.62, 7.59 Hz, 1H), 7.79 (d, J = 8.25 Hz, 2H), 7.91–7.99 (m, 3H), 8.62 (d, J = 7.92 Hz, 1H), 8.92 (d, J = 3.96 Hz, 1H) |

TABLE 7-continued

| | Structure | NMR |
|---|---|---|
| Example 41 | 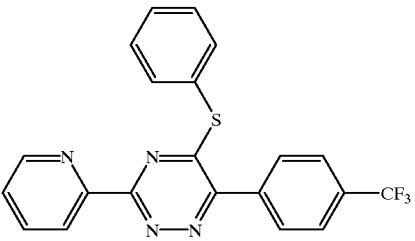 | (CDCl$_3$) δ: 7.38 (ddd, J = 1.32, 4.62, 7.58 Hz, 1H), 7.52–7.61 (m, 5H), 7.71 (dt, J = 1.65, 7.59 Hz, 1H), 7.81 (d, J = 7.92 Hz, 1H), 7.86 (d, J = 8.25 Hz, 2H), 8.09 (d, J = 7.92 Hz, 2H), 8.82 (d, J = 3.96 Hz, 1H) |
| Example 42 | 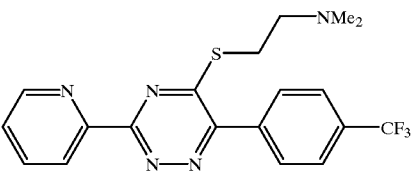 | (CDCl$_3$) δ: 2.31 (s, 6H), 2.70 (t, J = 6.93 Hz, 2H), 3.54 (t, J = 6.93 Hz, 2H), 7.49 (dd, J = 5.94, 6.27 Hz, 2H), 7.80 (d, J = 8.25 Hz, 2H), 7.93 (dt, J = 1.65, 7.59 Hz, 1H), 8.00 (d, J = 7.91 Hz, 2H), 8.57 (d, J = 7.92 Hz, 1H), 8.89 (d, J = 3.96 Hz, 1H) |
| Example 43 | 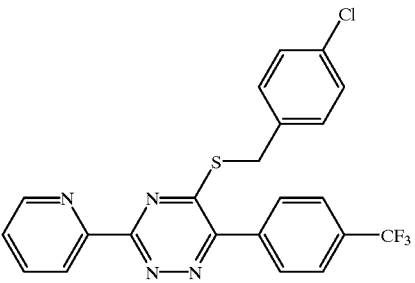 | (CDCl$_3$) δ: 4.57 (s, 2H), 7.25 (d, J = 8.58 Hz, 2H), 7.47 (d, J = 8.25 Hz, 2H), 7.52 (dd, J = 4.61, 8.91 Hz, 1H), 7.79 (d, J = 7.92 Hz, 2H), 7.91–7.98 (m, 3H), 8.60 (d, J = 7.91 Hz, 1H), 8.92 (d, J = 4.62 Hz, 1H) |
| Example 44 | 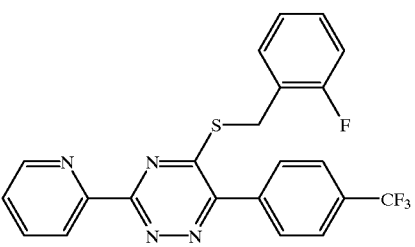 | (CDCl$_3$) δ: 4.67 (s, 2H), 7.01–7.08 (m, 2H), 7.21–7.30 (m, 2H), 7.52 (dd, J = 5.93, 6.27 Hz, 1H), 7.69 (t, J = 7.59 Hz, 1H), 7.79 (d, J = 8.58 Hz, 2H), 7.91–7.99 (m, 3H), 8.62 (d, J = 7.92 Hz, 1H), 8.93 (d, J = 3.96 Hz, 1H) |
| Example 45 | 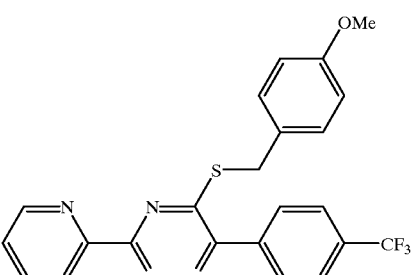 | (CDCl$_3$) δ: 3.76 (s, 3H), 4.58 (s, 2H), 6.82 (d, J = 8.58 Hz, 2H), 7.40 (d, J = 8.90 Hz, 2H), 7.50 (dd, J = 4.62, 7.59 Hz, 1H), 7.77 (d, J = 8.25 Hz, 2H), 7.90–7.98 (m, 3H), 8.60 (d, J = 8.24 Hz, 1H), 8.92 (d, J = 4.65 Hz, 1H) |

TABLE 8

| | Structure | NMR |
|---|---|---|
| Example 46 | 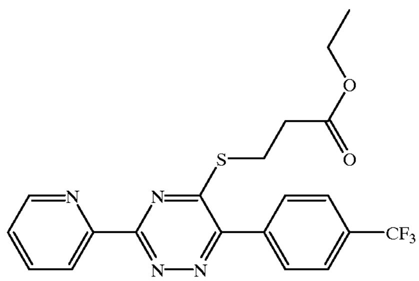 | (CDCl$_3$) δ: 1.26 (t, J = 6.93 Hz, 3H), 2.86 (t, J = 6.93 Hz, 2H), 3.63 (d, J = 6.93 Hz, 2H), 4.18 (q, J = 7.26 Hz, 2H), 7.50 (dd, J = 4.62, 6.60 Hz, 1H), 7.81 (d, J = 8.25 Hz, 2H), 7.89–8.00 (m, 3H), 8.54 (d, J = 7.92 Hz, 1H), 8.90 (d, J = 3.95 Hz, 1H) |
| Example 47 | 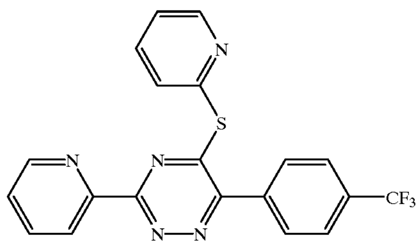 | (CDCl$_3$) δ: 7.38–7.44 (m, 2H), 7.72–7.81 (m, 5H), 7.93 (d, J = 7.92 Hz, 1H), 8.05 (d, J = 8.25 Hz, 2H), 8.70 (d, J = 4.95 Hz, 1H), 8.83 (d, J = 3.96 Hz, 1H) |
| Example 48 | 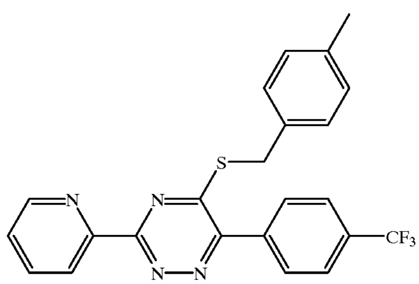 | (CDCl$_3$) δ: 2.30 (s, 3H), 4.58 (s, 2H), 7.10 (d, J = 7.92 Hz, 2H), 7.36 (d, J = 8.25 Hz, 2H), 7.51 (dd, J = 4.62, 7.59 Hz, 1H), 7.77 (d, J = 8.25 Hz, 2H), 7.90–7.98 (m, 3H), 8.59 (d, J = 7.91 Hz, 1H), 8.92 (d, J = 3.96 Hz, 1H) |
| Example 49 | 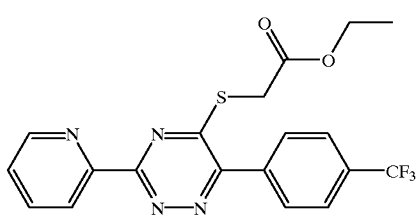 | (CDCl$_3$) δ: 1.26 (t, J = 6.60 Hz, 3H), 4.10 (s, 2H), 4.22 (q, J = 6.93 Hz, 2H), 7.50 (dd, J = 3.63, 7.59 Hz, 1H), 7.83 (d, J = 8.90 Hz, 2H), 7.92 (dt, J = 1.65, 7.59 Hz, 1H), 8.03 (d, J = 8.25 Hz, 2H), 8.52 (d, J = 7.92 Hz, 1H), 8.89 (d, J = 3.95 Hz, 1H) |
| Example 50 | 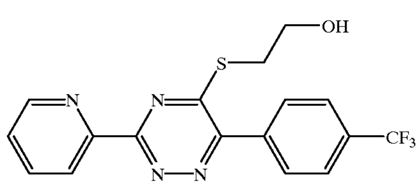 | (CDCl$_3$) δ: 3.59 (t, J = 5.94 Hz, 2H), 3.88 (t, J = 6.59 Hz, 2H), 7.65 (dd, J = 3.95, 7.59 Hz, 1H), 7.89 (d, J = 8.25 Hz, 2H), 8.03–8.60 (m, 3H), 8.62 (d, J = 7.92 Hz, 1H), 8.79–8.81 (m, 1H) |
| Example 51 | 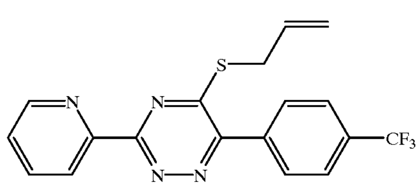 | (CDCl$_3$) δ: 4.05 (d, J = 6.93 Hz, 1H), 5.22 (d, J = 9.90 Hz, 1H), 5.45 (d, J = 16.83 Hz, 1H), 5.89–6.02 (m, 1H), 7.50 (dd, J = 4.62, 7.59 Hz, 1H), 7.81 (d, J = 8.25 Hz, 2H), 7.93 (dt, J = 1.65, 7.59 Hz, 1H), 8.00 (d, J = 7.91 Hz, 2H), 8.56 (d, J = 7.92 Hz, 1H), 8.90 (d, J = 5.60 Hz, 1H) |

TABLE 8-continued

| | Structure | NMR |
|---|---|---|
| Example 52 | 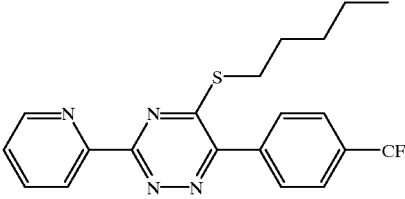 | (CDCl$_3$) δ: 0.90 (t, J = 6.93 Hz, 3H), 1.36–1.49 (m, 4H), 1.79 (qui, J = 7.59 Hz, 2H), 3.37 (t, J = 7.26 Hz, 2H), 7.49 (dd, J = 4.62, 8.91 Hz, 1H), 7.81 (d, J = 7.92 Hz, 2H), 7.93 (dt, J = 1.65, 7.92 Hz, 1H), 8.00 (d, J = 7.91 Hz, 2H), 8.53 (d, J = 7.92 Hz, 2H), 8.88–8.91 (m, 1H) |
| Example 53 | 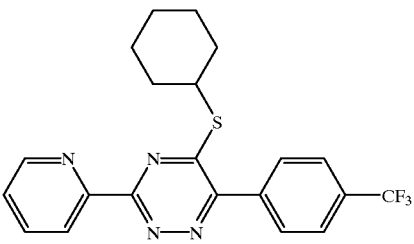 | (CDCl$_3$) δ: 1.3–1.9 (m, 8H), 2.1–2.2 (m, 2H), 4.1–4.2 (m, 1H), 7.49 (dd, J = 4.95, 7.59 Hz, 1H), 7.80 (d, J = 7.92 Hz, 2H), 7.89–7.99 (m, 3H), 8.48 (d, J = 7.92 Hz, 1H), 8.90 (d, J = 3.95 Hz, 1H) |

TABLE 9

| | Structure | NMR |
|---|---|---|
| Example 54 | 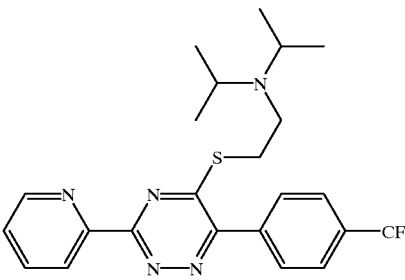 | (CDCl$_3$) δ: 1.00 (d, J = 6.27 Hz, 12H), 2.80 (t, J = 7.58 Hz, 2H), 3.07 (septet, J = 6.60 Hz, 2H), 3.40 (d, J = 7.58 Hz, 2H), 7.48 (dd, J = 4.95, 7.59 Hz, 1H), 7.80 (d, J = 7.92 Hz, 2H), 7.91 (t, J = 7.59 Hz, 1H), 8.00 (d, J = 7.91 Hz, 2H), 8.55 (d, J = 7.92 Hz, 2H), 8.87 (d, J = 3.96 Hz, 1H) |
| Example 55 | 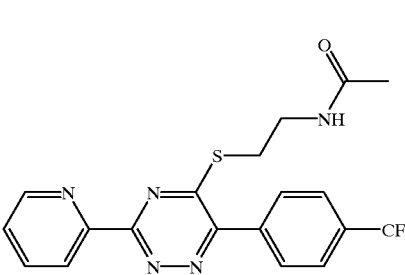 | (CDCl$_3$) δ: 1.97 (s, 3H), 3.48 (t, J = 6.27 Hz, 2H), 3.73 (q, J = 5.61 Hz, 2H), 7.55 (dd, J = 4.62, 7.58 Hz, 1H), 7.82 (d, J = 8.24 Hz, 2H), 7.88–8.03 (m, 4H), 8.76 (d, J = 7.91 Hz, 1H), 8.85 (d, J = 3.96 Hz, 1H) |
| Example 56 | 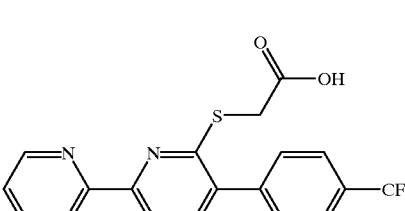 | (CDCl$_3$) δ: 4.21 (s, 2H), 7.63 (dd, J = 5.94, 7.59 Hz, 1H), 7.926 (d, J = 7.92 Hz, 2H), 8.04–8.10 (m, 3H), 8.61 (d, J = 7.91 Hz, 1H), 8.80 (d, J = 3.96 Hz, 1H) |

TABLE 9-continued

| Structure | NMR |
|---|---|
| Example 57 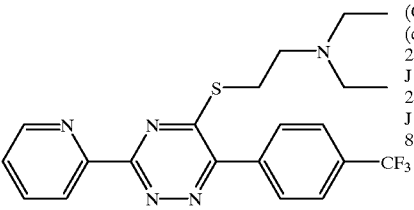 | (CDCl$_3$) δ: 1.03 (t, J = 6.93 Hz, 6H), 2.64 (q, J = 7.25 Hz, 4H), 2.84 (t, J = 7.59 Hz, 2H), 3.51 (t, J = 7.26 Hz, 2H), 7.49 (dd, J = 4.95, 7.59 Hz, 1H), 7.80 (d, J = 8.25 Hz, 2H), 7.92 (t, J = 7.92 Hz, 1H), 8.00 (d, J = 7.91 Hz, 2H), 8.58 (d, J = 7.92 Hz, 1H), 8.87 (d, J = 3.96 Hz, 1H) |
| Example 58 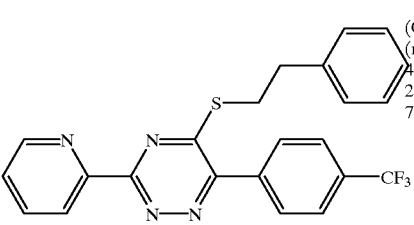 | (CDCl$_3$) δ: 3.05–3.11 (m, 2H), 3.58–3.64 (m, 2H), 7.24–7.35 (m, 5H), 7.51 (dd, J = 4.62, 7.59 Hz, 1H), 7.80 (d, J = 8.25 Hz, 2H), 7.89–8.00 (m, 3H), 8.57 (d, J = 7.92 Hz, 1H), 8.93 (d, J = 3.96 Hz, 1H). |
| Example 59 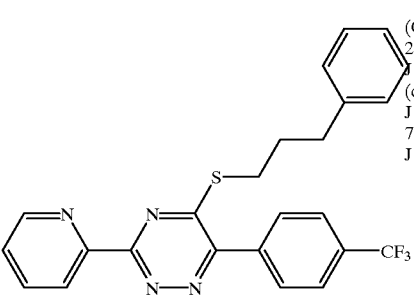 | (CDCl$_3$) δ: 2.13 (qui, J = 7.59 Hz, 2H), 2.81 (t, J = 7.25 Hz, 2H), 3.39 (t, J = 7.26 Hz, 2H), 7.17–7.30 (m, 5H), 7.49 (dd, J = 4.62, 7.59 Hz, 1H), 7.81 (d, J = 8.25 Hz, 2H), 7.91 (t, J = 7.92 Hz, 1H), 7.99 (d, J = 7.91 Hz, 2H), 8.45 (d, J = 7.91 Hz, 1H), 8.90 (d, J = 3.96 Hz, 1H) |
| Example 60 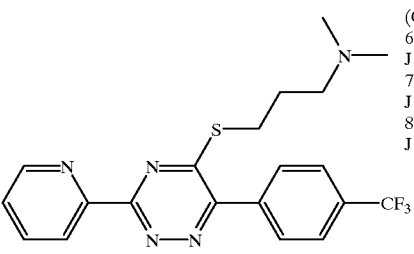 | (CDCl$_3$) δ: 1.93–1.98 (m, 2H), 2.23 (s, 6H), 2.44 (t, J = 6.93 Hz, 2H), 3.42 (t, J = 6.92 Hz, 2H), 3.37 (t, J = 7.26 Hz, 2H), 7.49 (dd, J = 4.62, 7.59 Hz, 1H), 7.81 (d, J = 8.25 Hz, 2H), 7.92 (t, J = 7.92 Hz, 1H), 8.00 (d, J = 8.24 Hz, 2H), 8.56 (d, J = 7.92 Hz, 1H), 8.89 (d, J = 3.96 Hz, 1H) |

Reference Example

Preparation of 3-(2-pyridyl)-6-(4-trifluoromethylphenyl)-1,2,4-triazin-5-one:

To a solution of 2-pyridylamidrazone (78.0 g, 573 mmol) in ethanol (800 ml) was added a solution of 4-trifluoromethylphenylpyrivic acid (125 g, 573 mmol, 1.0 eq.) in ethanol (350 ml), and the mixture was stirred at room temperature for one hour, and then heated under reflux for 9 hours. The reaction mixture was allowed to cool to room temperature, and the precipitated solid was collected by filtration. The solid was dispersed into hot chloroform (300 ml), and allowed to cool to room temperature. The precipitated yellow prisms were collected by filtration to give the title compound (119 g, 69%).

NMR(DMSO-d$_6$) 7.74 (dd, J=4.95, 7.59 Hz, 1H), 7.87 (d, J=8.58 Hz, 2H), 8.13 (dt, J=1.65, 7.58 Hz, 1H), 8.35 (m, 3H), 8.83 (d, J=4.62 Hz, 1H)

Preparation 1

Tablets are prepared from the following components.

| Components | Amount (mg/tablet) |
|---|---|
| Hydrochloride of the compound of Example 8 | 10 |
| Lactose | 72.5 |
| Corn Starch | 30 |
| Carboxymethyl cellulose calcium | 5 |
| Hydroxypropylcellulose (HPC-L) | 2 |
| Magnesium stearate | 0.5 |
| Total | 120 |

Each component is mixed, and tabletted to give tablets (each 120 mg).

Preparation 2

Injection Preparation is prepared from the following components.

| | |
|---|---|
| Hydrochloride of the compound of Example 8 | 1 mg |
| Physiological saline solution | 10 ml |

Under aseptic conditions, a solution consisting of the above components is sterilized by filtration, and filled into vials, which are washed and sterilized. The vials are sealed with a washed and sterilized rubber plugs, and sealed by flip off cap to give an injection preparation.

Experiment 1
LDL Receptor Increasing Activity

LDL receptors were detected from HepG2 cells which were cultured in a medium containing a lipoprotein-free serum, 25-hydroxycholesterol and a test compound, by the method disclosed in Journal of Biological Chemistry, vol. 266, p. 16764, 1991, except that Western-Blotting was carried out with using Anti-mouse Ig, Horseradish peroxidase (Amersham) instead of $^{125}$I-anti-mouse IgG, and LDL receptor was detected by ECL western-blotting detection system (Amersham).

The compound of Example 8 showed more excellent LDL receptor increasing activity at a dose of 1.2 μM compared with the control group.

Industrial Applicability

The compound (I) of the present invention increases the LDL receptor amount by increasing the expression of LDL receptor gene (amount of mRNA), thereby it can reduce the cholesterol level in the blood. Therefore, the compound (I) of the present invention is useful in the treatment of hyperlipidemia.

What is claimed is:

1. A method for promoting expression of LDL receptor gene, which comprises administering an effective amount of a 1,2,4-triazine compound of the formula (I):

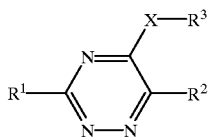

(I)

wherein $R^1$ is a substituted or unsubstituted phenyl group, or a substituted or unsubstituted heterocyclic group,
$R^2$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted alkyl group, or a substituted or unsubstituted alkenyl group,
X and $R^3$ are the following (i) or (ii):
(i) X is an oxygen atom or a sulfur atom, and $R^3$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted alkyl group, a substituted or unsubstituted cycloalkyl group, or a substituted or unsubstituted alkenyl group;
(ii) X is a group of the formula: —NR$^4$— (R$^4$ is a hydrogen atom, or a substituted or unsubstituted alkyl group), and $R^3$ is the same as defined above, or $R^4$ and $R^3$ may combine together with the nitrogen atom to which they bond to form a substituted or unsubstituted nitrogen-containing heterocyclic group, or a pharmaceutically acceptable salt thereof, to a mammal in need of such treatment.

2. The method according to claim 1, wherein $R^1$ is a substituted or unsubstituted nitrogen-containing aromatic cyclic group, and $R^2$ is a substituted or unsubstituted phenyl group.

3. The method according to claim 2, wherein $R^1$ is a substituted or unsubstituted pyridyl group.

4. The method according to claim 1, wherein the 1,2,4-triazine compound is selected from the following compounds, or a pharmaceutically acceptable salt thereof:

5-Allylamino-6-(2,4-dichlorophenyl)-3-(2-pyridyl)-1,2,4-triazine, 5-(t-Butylamino)-6-(2,4-dichlorophenyl)-3-(2-pyridyl)-1,2,4-triazine, 5-Benzylamino-6-(2,4-dichlorophenyl)-3-(2-pyridyl)-1,2,4-triazine, 6-(2,4-Dichlorophenyl)-5-cyclohexylamino-3-(2-pyridyl)-1,2,4-triazine, 5-Benzylamino-6-(4-methoxphenyl)-3-(2-pyridyl)-1,2,4-triazine, 5-(4-Fluorobenzylamino)-6-(4-methoxyphenyl)-3-(2-pyridyl)-1,2,4-triazine, 5-(4-Chlorobenzylamino)-6-(4-methoxyphenyl)-3-(2-pyridyl)-1,2,4-triazine, 5-Benzylamino-3-(2-pyridyl)-6-(4-trifluoromethylphenyl)-1,2,4-triazine, 5-(4-Fluorobenzylamino)-3-(2-pyridyl)-6-(4-trifluoromethylphenyl)-1,2,4-triazine, 5-(4-Methoxybenzylamino)-3-(2-pyridyl)-6-(4-trifluoromethylphenyl)-1,2,4-triazine, 5-(3-Methoxybenzylamino)-3-(2-pyridyl)-6-(4-trifluoromethylphenyl)-1,2,4-triazine, 5-(2-Methoxybenzylamino)-3-(2-pyridyl)-6-(4-trifluoromethylphenyl)-1,2,4-triazine, 5-(4-Dimethylaminobenzylamino)-3-(2-pyridyl)-6-(4-trifluoromethylphenyl)-1,2,4-triazine, 5-(4-Nitrobenzylamino)-3-(2-pyridyl)-6-(4-trifluoromethylphenyl)-1,2,4-triazine, 3-(2-Pyridyl)-5-(4-trifluoromethylbenzylamino)-6-(4-trifluoromethylphenyl)-1,2,4-triazine, 3-(2-pyridyl)-5-(2-pyridylmethylamino)-6-(4-trifluoromethylphenyl)-1,2,4-triazine, 3-(2-Pyridyl)-5-(3-pyridylmethylamino)-6-(4-trifluoromethylphenyl)-1,2,4-triazine, 3-(2-Pyridyl)-5-(4-pyridylmethylamino)-6-(4-trifluoromethylphenyl)-1,2,4-triazine, 5-Pentylamino-3-(2-pyridyl)-6-(4-trifluoromethylphenyl)-1,2,4-triazine, 5-(2-Ethoxyethylamino)-3-(2-pyridyl)-6-(4-trifluoromethylphenyl)-1,2,4-triazine, 3-(2-Pyridyl)-5-(2-thienylmethylamino)-6-(4-trifluoromethylphenyl)-1,2,4-triazine, 1-Phenyl-2-(3-(2-pyridyl)-6-(4-trifluoromethylphenyl)-1,2,4-triazin-5-ylamino)-propane-1,3-diol, 2-(Benzyl-(3-(2-pyridyl)-6-(4-trifluoromethylphenyl)-1,2,4-triazin-5-yl)amino)-1-ethanol, 5-(2-Phenylethylamino)-3-(2-pyridyl)-6-(4-trifluoromethylphenyl)-1,2,4-triazine, 5-(N-Methylbenzylamino)-3-(2-pryidyl)-6-(4-trifluoromethylphenyl)-1,2,4-triazine, 5-(4-Methylphenylamino)-3-(2-pryidyl)-6-(4-trifluoromethylphenyl)-1,2,4-triazine, 5-(3-Dimethylaminopropylamino)-3-(2-pryidyl)-6-(4-trifluoromethylphenyl)-1,2,4-triazine, 5-Morpholino-3-(2-pryidyl)-6-(4-trifluoromethylphenyl)-1,2,4-triazine, 5-(3-(2-Pyridyl)-6-(4-trifluoromethylphenyl)-1,2,4-triazin-5-ylamino)-pentan-1-ol, 2-(4-(3-(2-Pyridyl)-6-(4-trifluoromethylphenyl)-1,2,4-triazin-5-yl)-piperazin-1-yl)-ethanol, 2-Ethyl-2-(3-(2-pyridyl)-6-(4-trifluoromethylphenyl)-1,2,4-triazin-5-ylamino)-propane-1,3-diol, 5-Benzylamino-6-(4-chlorophenyl)-3-(2-pyridyl)-1,2,4-triazine, 5-Benzylamino-6-(4-chlorophenyl)-3-(3-pyridyl)-1,2,4-triazine, 5-Benzylamino-6-(4-chlorophenyl)-3-(4-pyridyl)-1,2,4-triazine, 5-Ethoxy-3-(2-pyridyl)-6-(4-trifluoromethylphenyl)-1,2,4-triazine, 5-Methoxy-3-(2-pyridyl)-6-(4-trifluoromethylphenyl)-1,2,4-triazine, 5-Benzyloxy-3-(2-pyridyl)-6-(4-trifluoromethylphenyl)-1,2,4-triazine, 5-Benzylthio-3-(2-pyridyl)-6-(4-trifluoromethylphenyl)-1,2,4-triazine, 5-Ethylthio-3-(2-pyridyl)-6-(4-trifluoromethylphenyl)-1,2,4-triazine, 5-Furfurylthio-3-(2-pyridyl)-6-(4-trifluoromethylphenyl)-1,2,4-triazine, 5-Phenylthio-3-(2-pyridyl)-6-(4-trifluoromethylphenyl)-1,2,4-triazine, 5-(2-Dimethylaminoethylthio)-3-(2-pyridyl)-6-(4-trifluoromethylphenyl)-1,2,4-triazine, 5-(4-Chlorobenzylthio)-3-(2-pyridyl)-6-(4-trifluoromethylphenyl)-1,2,4-triazine, 5-(2-Fluorobenzylthio)-3-(2-pyridyl)-6-(4-trifluoromethylphenyl)-1,2,4-triazine, 5-(4-Methoxybenzylthio)-3-(2-pyridyl)-6-(4-trifluoromethylphenyl)-1,2,4-triazine, 5-(4-Methylbenzylthio)-3-(2-pyridyl)-6-(4-trifluoromethylphenyl)-1,2,4-triazine, 5-(2-Ethoxycarbonylethylthio)-3-(2-pyridyl)-6-(4-trifluoromethylphenyl)-1,2,4-triazine, 3-(2-Pyridyl)-5-(2-pyridylthio)-6-(4-trifluoromethylphenyl)-1,2,4-triazine, 5-(Ethoxycarbonylmethylthio)-3-(2-pyridyl)-6-(4-trifluoromethylphenyl)-1,2,4-triazine, 2-(3-(2-Pyridyl)-6-(4-trifluoromethylphenyl)-1,2,4-triazin-5-ylsulfanyl)-ethanol, 5-Allylthio-3-(2-pyridyl)-6-(4-trifluoromethylphenyl)-1,2,4-triazine, 5-Pentylthio)-3-(2-pyridyl)-6-(4-trifluoromethylphenyl)-1,2,4-triazine, 5-Cyclohexylthio-3-(2-pyridyl)-6-(4-trifluoromethylphenyl)-1,2,4-triazine, 5-(2-Diisopropylaminoethylthio)-3-(2-pyridyl)-6-(4-trifluoromethylphenyl)-1,2,4-triazine, 5-(2-Acetylaminoethylthio)-3-(2-pyridyl)-6-(4-trifluoromethylphenyl)-1,2,4-triazine, (3-(2-pyridyl)-6-(4-trifluoromethylphenyl)-1,2,4-triazin-5-ylsulfanyl)acetic acid, 5-(2-Diethylaminoethylthio)-3-(2-pyridyl)-6-(4-trifluoromethylphenyl)-1,2,4-triazine, 5-(2-Phenylethylthio)-3-(2-pyridyl)-6-(4-trifluoromethylphenyl)-1,2,4-triazine, 5-(3-Phenylpropylthio)-3-(2-pyridyl)-6-(4-trifluoromethylphenyl)-1,2,4-triazine, and 5-(3-Dimethylaminopropylthio)-3-(2-pyridyl)-6-(4-trifluoromethylphenyl)-1,2,4-triazine.

5. A 1,2,4-triazine compound of the formula (I):

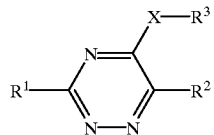

(I)

wherein $R^1$ is a substituted or unsubstituted nitrogen-containing aromatic cyclic group, $R^2$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted alkyl group, or a substituted or unsubstituted alkenyl group, X and $R^3$ are the following (i) or (ii):
(i) X is an oxygen atom or a sulfur atom, and $R^3$ is a substituted or unsubstituted phenyl group, a substituted or unsubstituted naphthyl group, a substituted or unsubstituted aralkyl group, a substituted or unsubstituted 5- to 6-membered aromatic heterocyclic group, a substituted or unsubstituted alkyl group, a substituted or unsubstituted cycloalkyl group, or a substituted or unsubstituted alkenyl group;
(ii) X is a group of the formula: —$NR^4$— ($R^4$ is a hydrogen atom, or a substituted or unsubstituted alkyl group), and $R^3$ is the same as defined above, or $R^4$ and $R^3$ may combine together with the nitrogen atom to which they bond to form a substituted or unsubstituted nitrogen-containing heterocyclic group, or a pharmaceutically acceptable salt thereof.

6. The 1,2,4-triazine compound according to claim 5, wherein $R^2$ is a substituted or unsubstituted phenyl group, or a pharmaceutically acceptable salt thereof.

7. The 1,2,4-triazine compound according to claim 5, which is selected from the following compounds, or a pharmaceutically acceptable salt thereof:

5-Allylamino-6-(2,4-dichlorophenyl)-3-(2-pyridyl)-1,2,4-triazine, 5-(t-Butylamino)-6-(2,4-dichlorophenyl)-3-(2-pyridyl)-1,2,4-triazine, 5-Benzylamino-6-(2,4-dichlorophenyl)-3-(2-pyridyl)-1,2,4-triazine, 6-(2,4-Dichlorophenyl)-5-cyclohexylamino-3-(2-pyridyl)-1,2,4-triazine, 5-Benzylamino-6-(4-methoxyphenyl)-3-(2-pyridyl)-1,2,4-triazine, 5-(4-Fluorobenzylamino)-6-(4-methoxyphenyl)-3-(2-pyridyl)-1,2,4-triazine, 5-(4-Chlorobenzylamino)-6-(4-methoxyphenyl)-3-(2-pyridyl)-1,2,4-triazine, 5-Benzylamino-3-(2-pyridyl)-6-(4-trifluoromethylphenyl)-1,2,4-triazine, 5-(4-Fluorobenzylamino)-3-(2-pyridyl)-6-(4-trifluoromethylphenyl)-1,2,4-triazine, 5-(4-Methoxybenzylamino)-3-(2-pyridyl)-6-(4-trifluoromethylphenyl)-1,2,4-triazine, 5-(3-Methoxybenzylamino)-3-(2-pyridyl)-6-(4-trifluoromethylphenyl)-1,2,4-triazine, 5-(2-Methoxybenzylamino)-3-(2-pyridyl)-6-(4-trifluoromethylphenyl)-1,2,4-triazine, 5-(4-Dimethylaminobenzylamino)-3-(2-pyridyl)-6-(4-trifluoromethylphenyl)-1,2,4-triazine, 5-(4-Nitrobenzylamino)-3-(2-pyridyl)-6-(4-trifluoromethylphenyl)-1,2,4-triazine, 3-(2-Pyridyl)-5-(4-trifluoromethylbenzylamino)-6-(4-trifluoromethylphenyl)-1,2,4-triazine, 3-(2-pyridyl)-5-(2-pyridylmethylamino)-6-(4-trifluoromethylphenyl)-1,2,4-triazine, 3-(2-Pyridyl)-5-(3-pyridylmethylamino)-6-(4-trifluoromethylphenyl)-1,2,4-triazine, 3-(2-Pyridyl)-5-(4-pyridylmethylamino)-6-(4-trifluoromethylphenyl)-1,2,4-triazine, 5-Pentylamino-3-(2-pyridyl)-6-(4-trifluoromethylphenyl)-1,2,4-triazine, 5-(2-Ethoxyethylamino)-3-(2-pyridyl)-6-(4-trifluoromethylphenyl)-1,2,4-triazine, 3-(2-Pyridyl)-5-(2-thienylmethylamino)-6-(4-trifluoromethylphenyl)-1,2,4-triazine, 1-Phenyl-2-(3-(2-pyridyl)-6-(4-trifluoromethylphenyl)-1,2,4-triazin-5-ylamino)-propane-1,3-diol, 2-(Benzyl-(3-(2-pyridyl)-6-(4-trifluoromethylphenyl)-1,2,4-triazin-5-yl)amino)-1-ethanol, 5-(2-Phenylethylamino)-3-(2-pyridyl)-6-(4-trifluoromethylphenyl)-1,2,4-triazine, 5-(N-Methylbenzylamino)-3-(2-pyridyl)-6-(4-trifluoromethylphenyl)-1,2,4-triazine, 5-(4-Methoxyphenylamino)-3-(2-pyridyl)-6-(4-trifluoromethylphenyl)- 1,2,4-triazine, 5-(3-Dimethylaminopropylamino)-3-(2-pyridyl)-6-(4-trifluoromethylphenyl)-1,2,4-triazine, 5-Morpholino-3-(2-pyridyl)-6-(4-trifluoromethylphenyl)-1,2,4-triazine, 5-(3-(2-Pyridyl)-6-(4-trifluoromethylphenyl)-1,2,4-triazin-5-ylamino)-pentan-1-ol, 2-(4-(3-(2-Pyridyl)-6-(4-trifluoromethylphenyl)-1,2,4-triazin-5-yl)-piperazin-1-yl)-ethanol, 2-Ethyl-2-(3-(2-pyridyl)-6-(4-trifluoromethylphenyl)-1,2,4-triazin-5-ylamino)-propane-1,3-diol, 5-Benzylamino-6-(4-chlorophenyl)-3-(2-pyridyl)-1,2,4-triazine, 5-Benzylamino-6-(4-chlorophenyl)-3-(3-pyridyl)-1,2,4-triazine, 5-Benzylamino-6-(4-chlorophenyl)-3-(4-pyridyl)-1,2,4-triazine, 5-Ethoxy-3-(2-pyridyl)-6-(4-trifluoromethylphenyl)-1,2,4-triazine, 5-Methoxy-3-(2-pyridyl)-6-(4-trifluoromethylphenyl)-1,2,4-triazine, 5-Benzyloxy-3-(2-pyridyl)-6-(4-trifluoromethylphenyl)-1,2,4-triazine, 5-Benzylthio-3-(2-pyridyl)-6-(4-trifluoromethylphenyl)-1,2,4-triazine, 5-Ethylthio-3-(2-pyridyl)-6-(4-trifluoromethylphenyl)-1,2,4-triazine, 5-Furfurylthio-3-(2-pyridyl)-6-(4-trifluoromethylphenyl)-1,2,4-triazine, 5-Phenylthio-3-(2-pyridyl)-6-(4-trifluoromethylphenyl)-1,2,4-triazine, 5-(2-Dimethylaminoethylthio)-3-(2-pyridyl)-6-(4-trifluoromethylphenyl)-1,2,4-triazine, 5-(4-Chlorobenzylthio)-3-(2-pyridyl)-6-(4-trifluoromethylphenyl)-1,2,4-triazine, 5-(2-Fluorobenzylthio)-3-(2-pyridyl)-6-(4-trifluoromethylphenyl)-1,2,4-triazine, 5-(4-Methoxybenzylthio)-3-(2-pyridyl)-6-(4-trifluoromethylphenyl)-1,2,4-triazine, 5-(4-Methylbenzylthio)-3-(2-pyridyl)-6-(4-trifluoromethylphenyl)-1,2,4-triazine, 5-(2-Ethoxycarbonylethylthio)-3-(2-pyridyl)-6-(4-trifluoromethylphenyl)-1,2,4-triazine, 3-(2-Pyridyl)-5-(2-pyridylthio)-6-(4-trifluoromethylphenyl)-1,2,4-triazine, 5-Ethoxycarbonylmethylthio-3-(2-pyridyl)-6-(4-trifluoromethylphenyl)-1,2,4-triazine, 2-(3-(2-Pyridyl)-6-(4-trifluoromethylphenyl)-1,2,4-triazin-5-ylsulfanyl)-ethanol, 5-Allylthio-3-(2-pyridyl)-6-(4-trifluoromethylphenyl)-1,2,4-triazine, 5-Pentylthio-3-(2-pyridyl)-6-(4-trifluoromethylphenyl)-1,2,4-triazine, 5-Cyclohexylthio-3-(2-pyridyl)-6-(4-trifluoromethylphenyl)-1,2,4-triazine, 5-(2-Diisopropylaminoethylthio)-3-(2-pyridyl)-6-(4-trifluoromethylphenyl)-1,2,4-triazine, 5-(2-Acetylaminoethylthio)-3-(2-pyridyl)-6-(4-trifluoromethylphenyl)-1,2,4-triazine, (3-(2-Pyridyl)-6-(4-trifluoromethylphenyl)-1,2,4-triazin-5-ylsulfanyl)acetic acid, 5-(2-Diethylaminoethylthio)-3-(2-pyridyl)-6-(4-trifluoromethylphenyl)-1,2,4-triazine, 5-(2-Phenylethylthio)-3-(2-pyridyl)-6-(4-trifluoromethylphenyl)-1,2,4-triazine, 5-(3-Phenylpropylthio)-3-(2-pyridyl)-6-(4-trifluoromethylphenyl)-1,2,4-triazine, and 5-(3-Dimethylaminopropylthio)-3-(2-pyridyl)-6-(4-trifluoromethylphenyl)-1,2,4-triazine.

8. The method according to any one of claims 1 to 4, which is a treatment of hyperlipidemia or arteriosclerosis.

* * * * *